US010551345B2

(12) United States Patent
Lau

(10) Patent No.: US 10,551,345 B2
(45) Date of Patent: *Feb. 4, 2020

(54) POLY AND COPOLY(N-VINYLAMIDE)S AND THEIR USE IN CAPILLARY ELECTROPHORESIS

(71) Applicant: Applied Biosystems, LLC, Carlsbad, CA (US)

(72) Inventor: Aldrich N. K. Lau, Palo Alto, CA (US)

(73) Assignee: APPLIED BIOSYSTEMS, LLC, Carlsbad, CA (US)

( * ) Notice: Subject to any disclaimer, the term of this patent is extended or adjusted under 35 U.S.C. 154(b) by 182 days.

This patent is subject to a terminal disclaimer.

(21) Appl. No.: 15/595,439

(22) Filed: May 15, 2017

(65) Prior Publication Data
US 2017/0356877 A1    Dec. 14, 2017

Related U.S. Application Data

(60) Division of application No. 14/148,401, filed on Jan. 6, 2014, now Pat. No. 9,671,367, which is a continuation of application No. 12/616,748, filed on Nov. 11, 2009, now abandoned, which is a continuation of application No. 10/843,114, filed on May 11, 2004, now abandoned.

(60) Provisional application No. 60/471,519, filed on May 15, 2003.

(51) Int. Cl.
G01N 27/453    (2006.01)
G01N 27/447    (2006.01)
C08F 20/54     (2006.01)

(52) U.S. Cl.
CPC . G01N 27/44747 (2013.01); G01N 27/44752 (2013.01); C08F 20/54 (2013.01)

(58) Field of Classification Search
CPC ........ G01N 27/44752; G01N 27/44747; C08F 20/54
See application file for complete search history.

(56) References Cited

U.S. PATENT DOCUMENTS

| | | |
|---|---|---|
| 3,718,717 A | 2/1973 | Legomann |
| 4,330,653 A | 5/1982 | Klippert et al. |
| 4,548,498 A | 10/1985 | Folestad et al. |
| 4,675,300 A | 6/1987 | Zare et al. |
| 4,772,359 A | 9/1988 | Linhart |
| 4,808,683 A | 2/1989 | Itagaki et al. |
| 4,837,446 A | 6/1989 | Renard |
| 4,865,707 A | 9/1989 | Karger et al. |
| 4,908,112 A | 3/1990 | Pace |
| 4,997,537 A | 3/1991 | Karger et al. |
| 5,002,587 A | 3/1991 | Berendt |
| 5,015,350 A | 5/1991 | Wiktorowicz |
| 5,100,952 A | 3/1992 | Hoskin et al. |
| 5,126,021 A | 6/1992 | Grossman |
| 5,126,395 A | 6/1992 | End et al. ................ 524/801 |
| 5,181,999 A | 1/1993 | Wiktorowicz |
| 5,192,412 A | 3/1993 | Kambara et al. |
| 5,264,101 A | 11/1993 | Demorest et al. |
| 5,384,024 A | 1/1995 | Moring et al. |
| 5,468,365 A | 11/1995 | Menchen et al. |
| 5,501,770 A | 3/1996 | Sarkar et al. |
| 5,503,722 A | 4/1996 | Guttman .................. 204/450 |
| 5,512,645 A | 4/1996 | Sawayama et al. |
| 5,530,069 A | 6/1996 | Neff et al. |
| 5,552,028 A | 9/1996 | Madabhushi et al. |
| 5,629,184 A | 5/1997 | Goldenberg et al. |
| 5,630,850 A | 5/1997 | Schaffluetzel et al. |
| 5,916,426 A | 6/1999 | Madabhushi et al. |
| 6,013,165 A | 1/2000 | Wiktorowicz et al. |
| 6,028,233 A | 2/2000 | Colle et al. |
| 6,057,106 A | 5/2000 | Updyke |
| 6,060,566 A | 5/2000 | Denzinger et al. |
| 6,107,531 A | 8/2000 | Colle et al. |
| 6,124,396 A | 9/2000 | Hahn et al. |
| 6,228,487 B1 | 5/2001 | Howard et al. |
| 6,273,998 B1 | 8/2001 | Kuo et al. |
| 6,319,971 B1 | 11/2001 | Kelland et al. |
| 6,794,458 B2 | 9/2004 | Haddad |
| 6,939,451 B2 | 9/2005 | Zhao |
| 9,671,367 B2 * | 6/2017 | Lau ................ G01N 27/44747 |

(Continued)

FOREIGN PATENT DOCUMENTS

DE    1933 844    5/1970
EP    0 044 995   2/1982
(Continued)

OTHER PUBLICATIONS

Extended European Search Report of the European Patent Office, application No. PCT/EP 09/00227.0-2109, (Mar. 20, 2009) (5 pages).
Standard Practice for General Techniques of Liquid Chromatography-Infrared (LC/IR) and Size Exclusion Chromatography-Infrared (SEC/IR) Analyses. ASTM Designation: E2106-00: (2000) 1-7.
Adler. Cross-linking of Polymers by Radiation. Science 141 (1963) 321-9.
Akashi et al. Novel Hydrogels for Electrophoresis. Chromatography 15 (1994) 108-9 (in Japanese, with English abstract).
Anufrieva et al. Macromolecular Collapse of Water-soluble Polymers Under the Effect of Phenol. Vysokomol. Soedin, Ser. A Ser. B 40 (1998) 1870-5 (in Russian, with English abstract).

(Continued)

Primary Examiner — Alexander S Noguerola

(57) ABSTRACT

The invention relates generally to polymers and copolymers comprising N-vinylamide-type monomers, their preparation, and compositions, such as electrophoresis separation media, containing the same; to supports, such as capillaries, containing these polymers; and methods for separating a mixture of biomolecules, especially polynucleotides, using capillary electrophoresis. Separation media comprising such polymers yield advantageous performance in the analysis and separation of biomolecules by capillary electrophoresis.

25 Claims, No Drawings

(56) References Cited

U.S. PATENT DOCUMENTS

| | | | |
|---|---|---|---|
| 2001/0023827 A1 | 9/2001 | Liu et al. | 204/605 |
| 2002/0029968 A1 | 3/2002 | Tan et al. | |

FOREIGN PATENT DOCUMENTS

| | | |
|---|---|---|
| EP | 0 729 980 | 9/1996 |
| JP | 59-039399 | 3/1984 |
| JP | 62-199872 | 9/1987 |
| JP | 63-162274 | 7/1988 |
| JP | 64-015637 | 3/1989 |
| JP | 02-304052 | 12/1990 |
| JP | 04-264182 | 9/1992 |
| JP | 06-173168 | 6/1994 |
| JP | 06-184251 | 7/1994 |
| JP | 06-184386 | 7/1994 |
| JP | 9-236580 | 9/1997 |
| JP | 09/236580 | 9/1997 |
| JP | 11-129609 | 5/1999 |
| JP | 2000-136351 | 5/2000 |
| JP | 2001-002937 | 1/2001 |
| JP | 2001-081670 | 3/2001 |
| JP | 2002-019274 | 1/2002 |
| JP | 2002-020569 | 1/2002 |
| SU | 278112 | 8/1970 |
| WO | WO 96/41784 | 12/1996 |
| WO | WO 00/42423 | 7/2000 |
| WO | WO 01/29098 | 4/2001 |
| WO | WO 2001/081906 | 11/2001 |
| WO | WO 02/24313 | 3/2002 |

OTHER PUBLICATIONS

Campbell et al. Polystyrene Particles with Surface Amino Groups. J. Dispersion Sci. Technol. 19 (1998) 785-804.
Chen et al. Investigations on Vinylene Carbonate. III. Monomer Reactivity Ratios and Characterization ofVinylene Carbonate-N-Vinyl-N-Methylacetamide Copolymers. J. Appl. Polym. Sci.: Appl. Polym. Symp. 48 (1991) 545-60.
Costello et al. Copolymers. Kirk-0thmer Encyc. of Chem. Technol., John Wiley & Sons, New York, 4th Ed. 7 (1993) 349-81.
Cutler et al. Chemical Characterization of Antiwear Films Generated by Tris-[p(perfluoroalkylether)phenyl] Phosphine Using X-ray Absorption Spectroscopy. Wear 236 (1999) 165-78.
Drossman et al. High-Speed Separations of DNA Sequencing Reactions by Capillary Electrophoresis. Anal. Chem. 62 (1990) 900-903.
Engelhardt et al. Preparation and Stability Tests for Polyacrylamide-Coated Capillaries for Capillary Electrophoresis. Journal of Chromatography A 716 (1995) 27-33.
Gartin. Electrophoretic Methods. Introduction to Biophysical Methods for Protein and Nucleic Acid Research, Dept. of Biochem., Univ. of Connecticut Health Center, Academic Press (1995) 100-104.
Grifin. Emulsions. Kirk-Othmer Encyc. of Chem. Technol., John Wiley & Sons, New York, 3rd Ed. 8 (1979) 909-19.
Horvath et al. Polymer Wall Coating for Capillary Electrophoresis. Electrophoresis 22 (2001) 644-655.
Huang et al. DNA Sequencing Using Capillary Array Electrophoresis. Anal. Chem. 64 (1992) 2149-54.
Ito et al. Research and Development of Bearings for Special Environments. Motion & Control 4 (1998) 13-21.
Juranicova et al. Inverse Microemulsion Polymerization of Acrylamide in the Presence of N,N-Dimethylacrylamide. Die Angewandte Makromolekulare Chemie 258 (Nr. 4502) (1998) 27-31.
Karis et al. Rheology of Perflouropolyethers with Polar End Groups. The Society of Rheology: 72nd Annual Meeting, Paper CG3 (2001) (abstract only).
Kim et al. Copolymerization of N-vinylurea and Vinyl Acetate. II. Solvent Effects in Radical Copolymerization. Taehan Hwahakhoe Chi 24 (1980) 80-5 (1980) (in Korean, with English abstract).
Liang et al. Formation of Concentration Gradient and its Application to DNA Capillary Electrophoresis. Electrophoresis 21 (2000) 3600-08.
Lipp et al. Acrylamide Polymers. Kirk-0thmer Encyc. of Chem. Technol., John Wiley & Sons, New York, 4th Ed. 1 (1991) 266-87.
Odian. Principles of Polymerization. McGraw-Hill Book Co., New York (1970) 366, 633.
Perry. Petroleum and Complex-Mixture Distillation. Perry's Chemical Engineer's Handbook, 6th Ed. (1984) 1371-81.
Quesada et al. Replaceable Polymers for DNA Sequencing by Capillary Electrophoresis. Methods in Molecular Biology 162 (2001) 139-49.
Quesada et al. Replaceable Polymers in DNA Sequencing by Capillary Electrophoresis. Current Opinion in Biotechnology (1997) 82-93.
Righetti et al. The State of the Art of Dynamic Coatings. Electrophoresis 22 (2001) 603-611.
Stannett et al. Polymerization by High-energy Radiation. Comprehensive Polymer Science, Chain Polymerization II, Pergamon Press 4 (1989) 317-336.
Sudor et al. New Block-Copolymer Theremoassociating Matrices for DNA Sequencing: Effect of Molecular Structure on Rheology and Resolution. Electrophoresis 22 (2001) 720-728.
Swerdlow et al. Capillary Gel Electrophoresis for Rapid, High Resolution DNA Sequencing. Nucleic Acids Research 18 (1990) 1415-19.
Thomas. Acrylamide Polymers. Encyc. of Polymer Science and Technology, Plastics, Resins, Rubbers, Fibers, John Wiley & Sons 1 (1964) 177-97.
Viovy et al. Principles of Size-Based Separations in Polymer Solutions. Capillary Electrophoresis in Analytical Biotechnology 478-508.
Williams. The Analysis of DNA Restriction Fragments and Polymerase Chain Reaction Products by Dynamic Sieving Electrophoresis. Methods 4 (1992) 227-232.
Yau. New Polymer Characterization Capabilities Using Size Exclusion Chromatography with On-Line Molecular Weight-Specific Detectors. Chemtracts-Macromolecular Chemistry 1 (1990) 1-36.
Albarghouthi et al. Polymeric Matrices for DNA Sequencing by Capillary Electrophoresis. Electrophoresis 21 (2000) 4096-4111.
Barton et al. Radical Polymerization in Disperse Systems. Ellis Horwood (1994) 186-215.
Bode. The Use of Liquid Polyacrylamide in Electrophoresis I. Mixed Gels Composed of Agar-Agar and Liquid Polyacrylamide. Anal. Biochem. 83 (1977) 204-210.
Bode. The Use of Liquid Polyacrylamide in Electrophoresis II. Relationship Between Gel Viscosity and Molecular Sieving. Anal. Biochem. 83 (1977) 364-371.
Bode. The Use of Liquid Polyacrylamide in Electrophoresis III. Properties of Liquid Polyacrylamide in the Presence of Cellulose Acetate. Anal. Biochem. 92 (1979) 99-110.
Candau et al. Kinetic Study of the Polymerization of Acrylamide in Inverse Microemulsion. Journal of Polymer Science: Polymer Chemistry Edition 23 (1985) 193-214.
Faust. Initiators (Cationic). Kirk-0thmer Encyc. of Chem. Technol., John Wiley & Sons, New York, 4th Ed. 14 (1995) 476-82.
Hamada. Rotational Isomeric State Study of Molecular Dimensions and Elasticity of Perfluoropolyethers: Differences Between Demnum-, Fomblin-, and Krvtox-type Main Chains. Phys. Chem. Chem. Phys. 2 (1999) 115-22.
Harrison et al. Micromachining a Miniaturized Capillary Electrophoresis-Based Chemical Analysis System on a Chip. Science 261 (1993) 895-97.
Hjerten et al. High-Performance Electrophoresis of Acidic and Basic Low-Molecular-Weight Compounds and of Proteins in the Presence of Polymers and Neutral Surfactants. J. Liquid Chromatography 12 (1989) 2471-77.
Liu et al. Optimization of High-Speed DNA Sequencing on Microfabricated Capillary Electrophoresis Channels. Anal. Chem. 71 (1999) 566-73.
Lynn, Jr. et al. Surfactants. Kirk-Othmer Encyc. of Chem. Technol., John Wiley & Sons, New York, 4th Ed. 23 (1997) 478-541.
McGinniss. Radiation Curing. Kirk-0thmer Encyc. of Chem. Technol., John Wiley & Sons, New York, 4th Ed. 20 (1996) 831-59.

(56) References Cited

OTHER PUBLICATIONS

Pross et al. The Inverse Emulsion Polymerization of Acrylamide with Pentaerythritolmyristate as Emulsifier 1. Experimental Studies. Polymer International 45 (1998) 22-26.
Quirk et al. Initiators (Anionic). Kirk-Othmer Encyc. of Chem. Technol., John Wiley & Sons, New York, 1995, 4th Ed. 14 (1995) 461-76.
Sanchez et al. Initiators (Free-Radical). Kirk-0thmer Encyc. of Chem. Technol., John Wiley & Sons, New York, 4th Ed. 14 (1995) 431-60.
Seiler et al. Planar Glass Chips for Capillary Electrophoresis: Repetitive Sample Injection, Quantitation, and Separation Efficiency. Anal. Chem. 65 (1993) 1481-88.
Sheppard et al. Initiators. Kirk-0thmer Encyc. of Chem. Technol., John Wiley & Sons, New York, 3rd Ed. 13 (1981) 355, 367-73.
Tietz et al. Advances in DNA Electrophoresis in Polymer Solutions. Electrophoresis 13 (1992) 614-16.
Woolley et al. Ultra-High-Speed DNA Sequencing Using Capillary Electrophoresis Chips. Anal. Chem. 67 (1995) 3676-80.
Wyatt. Light Scattering and the Absolute Characterization of Macromolecules. Analytica Chimica Acta 272 (1993) 1-40.
C1 EP09000227.0, Office action dated Apr. 12, 2010.
C2 EP09000227.0 Office Action dated Nov. 20, 2009.
C3 EP090002270 Office Action dated Aug. 24, 2010.
C4 KR 10-2005-7021809 Office Action dated Mar. 2, 2011.
C5 JP2006-532979 Translation of Office Action dated Oct. 8, 2010.
International Preliminary Report of Patentability and Written Opinion, completed on Jun. 29, 2005, for PCT Application No. PCT/US2004/014831, filed May 12, 2004.
International Search Report, dated Oct. 13, 2004, for PCT Application No. PCT/US2004/014831, filed May 12, 2004.
Official Communication dated Mar. 15, 2006, for European Patent Application No. 04 751 975.6.
Official Communication dated Mar. 14, 2008, for European Patent Application No. 04 751 975.6.
Official Communication dated Nov. 20, 2009, for European Patent Application No. 09 000 227.0.
File History of U.S. Appl. No. 14/148,401, filed Jan. 6, 2014.

* cited by examiner

POLY AND COPOLY(N-VINYLAMIDE)S AND THEIR USE IN CAPILLARY ELECTROPHORESIS

This application claims the benefit of U.S. provisional application No. 60/471,519 filed May 15; 2003, the disclosure of the provisional application being incorporated by reference herein in its entirety.

1. FIELD OF THE INVENTION

The invention relates generally to polymers and copolymers comprising a N-vinylamide-type monomer, their preparation, and compositions useful for electrophoresis separation comprising the same; and to supports, such as capillaries, containing these polymers and methods for separating a mixture of biomolecules, especially polynucleotides, using capillary electrophoresis.

2. BACKGROUND OF THE INVENTION

Capillary electrophoresis ("CE") is a widely used analytical method because of several technical advantages that it provides, namely: (i) capillaries containing a separation medium have high surface-to-volume ratios and dissipate heat efficiently which, in turn, permits high-voltage fields to be used for rapid separations; (ii) minimal sample volume is needed; (iii) superior resolution is attainable; and (iv) the technique can easily be automated, e.g., Camilleri, Ed., *Capillary Electrophoresis: Theory and Practice* (CRC Press, Boca Raton, 1993); Grossman et al., Eds., *Capillary Electrophoresis* (Academic Press, San Diego, 1992). Because of these advantages, there has been great interest in applying CE to the separation of biomolecules, particularly in nucleic acid analysis. The need for rapid and accurate separation of nucleic acids, particularly deoxyribonucleic acid ("DNA"), arises in the analysis of polymerase chain reaction products and DNA sequencing fragment analysis, e.g., Williams, *Methods* 4:227-232 (1992); Drossman et al., *Anal. Chem.*, 62:900-903 (1990); Huang et al., *Anal. Chem.*, 64:2149-2154 (1992); Swerdlow et al., *Nucleic Acids Research*, 18:1415-1419 (1990).

There remains, however, a need for polymers and copolymers that are effective for separating, e.g., a mixture of biomolecules, especially polynucleotides, using CE, and compositions comprising a polymer useful for the same.

The citation of any reference in Section 2 of this application is not an admission that the reference is prior art to the application.

3. SUMMARY OF THE INVENTION

A first embodiment of the invention relates to a polymer having the form poly($M_1^x M_2^y$) and a salts thereof comprising one or more monomers of type $M_1$ and optionally one or more monomers of type $M_2$, wherein:

(a) each monomer in the polymer is of type $M_1$ or $M_2$;

(b) x is an integer ranging from 1 to 5 and represents the number of monomer subtypes of type $M_1$ that are present in the polymer;

(c) y is an integer ranging from 0 to 5 and represents the number of monomer subtypes of type $M_2$ that are present in the polymer;

(d) each monomer subtype of type $M_1$ in the polymer independently has the formula (I):

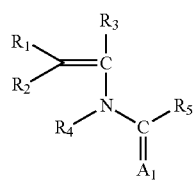

(I)

where each $A_1$ is independently =O, =S or =$NX_1$;
each of $R_1$, $R_2$, $R_3$ and $R_4$ is independently —H, —($C_1$-$C_{10}$ alkyl), —($C_3$-$C_8$ cycloalkyl), -(aryl), -(5- to 10-membered heteroaryl), —($C_1$-$C_{10}$ alkyl)(aryl) or -(aryl)($C_1$-$C_{10}$ alkyl);
each $R_5$ is independently —(H), —($C_1$-$C_{10}$ alkyl), —($C_1$-$C_{10}$ heteroalkyl), —($C_3$-$C_8$ cycloalkyl), -(3- to 8-membered heterocycloalkyl), -(aryl), -(5- to 10-membered heteroaryl), —($C_1$-$C_{10}$ alkyl)($C_3$-$C_8$ cycloalkyl), —($C_3$-$C_8$ cycloalkyl)($C_1$-$C_{10}$ alkyl), —($C_1$-$C_{10}$ heteroalkyl)($C_3$-$C_8$ cycloalkyl), —($C_3$-$C_8$ cycloalkyl)($C_1$-$C_{10}$ heteroalkyl), —($C_1$-$C_{10}$ alkyl)(3- to 8-membered heterocycloalkyl), -(3- to 8-membered heterocycloalkyl)($C_1$-$C_{10}$ alkyl), —($C_1$-$C_{10}$ heteroalkyl)(3- to 8-membered heterocycloalkyl), -(3- to 8-membered heterocycloalkyl)($C_1$-$C_{10}$ heteroalkyl), —($C_1$-$C_{10}$ alkyl)(aryl), -(aryl)($C_1$-$C_{10}$ alkyl), —($C_1$-$C_{10}$ heteroalkyl)(aryl), -(aryl)($C_1$-$C_{10}$ heteroalkyl), —($C_1$-$C_{10}$ alkyl)(5- to 10-membered heteroaryl), -(5- to 10-membered heteroaryl)($C_1$-$C_{10}$ alkyl), —($C_1$-$C_{10}$ heteroalkyl)(5- to 10-membered heteroaryl), -(5- to 10-membered heteroaryl)($C_1$-$C_{10}$ heteroalkyl), —($C_1$-$C_4$ alkyl)$_p$NH$_2$, —($C_1$-$C_4$ alkyl)$_p$CONH$_2$, —($C_1$-$C_4$ alkyl)NHCONH$_2$, —($C_1$-$C_4$ alkyl)NHCOH or —($C_1$-$C_4$ alkyl)$_p$NHCOCH$_3$, where each p is 0 or 1; and
each $X_1$ is independently —H, —($C_1$-$C_{10}$ alkyl), —($C_3$-$C_8$ cycloalkyl), -(aryl), -(5- to 10-membered heteroaryl), —($C_1$-$C_{10}$ alkyl)(aryl), -(aryl)($C_1$-$C_{10}$ alkyl), —($C_1$-$C_4$ alkyl)$_p$NH$_2$, —($C_1$-$C_4$ alkyl)$_p$CONH$_2$, —($C_1$-$C_4$ alkyl)NHCONH$_2$, —($C_1$-$C_4$ alkyl)$_p$NHCOH or —($C_1$-$C_4$ alkyl)$_p$NHCOCH$_3$, where each p is 0 or 1; and (e) when y is not zero, each monomer subtype of type $M_2$ in the polymer is independently:
1-vinyl-pyrrolidine-2,5-dione;
3-vinyl-oxazolidin-2-one;
1-vinyl-imidazolidin-2-one;
4-vinyl-morpholin-3,5-dione;
4-vinyl-morpholin-3-one;
4-vinyl-morpholine;
2-vinyl-1,3-dioxolane;
2-vinylene carbonate;
methoxyethylene;
vinyl acetate;
vinyl alcohol;
a monomer of formula (II):

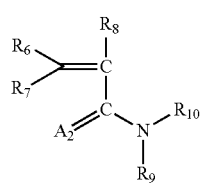

(II)

where each $A_2$ is independently =O, =S or =NX$_2$;
each of $R_6$, $R_7$, $R_8$ and $R_9$ is independently —H, —(C$_1$-C$_{10}$ alkyl), —(C$_3$-C$_8$ cycloalkyl), -(aryl), -(5- to 10-membered heteroaryl), —(C$_1$-C$_{10}$ alkyl)(aryl) or -(aryl)(C$_1$-C$_{10}$ alkyl);
each $R_{10}$ is independently —H, —OH, —(C$_1$-C$_{10}$ alkyl), —(C$_1$-C$_{10}$ heteroalkyl), —(C$_3$-C$_8$ cycloalkyl), -(3- to 8-membered heterocycloalkyl), -(aryl), -(5- to 10-membered heteroaryl), —(C$_1$-C$_{10}$ alkyl)(C$_3$-C$_8$ cycloalkyl), —(C$_3$-C$_8$ cycloalkyl)(C$_1$-C$_{10}$ alkyl), —(C$_1$-C$_{10}$ heteroalkyl)(C$_3$-C$_8$ cycloalkyl), —(C$_3$-C$_8$ cycloalkyl)(C$_1$-C$_{10}$ heteroalkyl), —(C$_1$-C$_{10}$ alkyl)(3- to 8-membered heterocycloalkyl), -(3- to 8-membered heterocycloalkyl)(C$_1$-C$_{10}$ alkyl), —(C$_1$-C$_{10}$ heteroalkyl)(3- to 8-membered heterocycloalkyl), -(3- to 8-membered heterocycloalkyl)(C$_1$-C$_{10}$ heteroalkyl), —(C$_1$-C$_{10}$ alkyl)(aryl), -(aryl)(C$_1$-C$_{10}$ alkyl), —(C$_1$-C$_{10}$ heteroalkyl)(aryl), -(aryl)(C$_1$-C$_{10}$ heteroalkyl), —(C$_1$-C$_{10}$ alkyl)(5- to 10-membered heteroaryl), -(5- to 10-membered heteroaryl)(C$_1$-C$_{10}$ alkyl), —(C$_1$-C$_{10}$ heteroalkyl)(5- to 10-membered heteroaryl), -(5- to 10-membered heteroaryl)(C$_1$-C$_{10}$ heteroalkyl), —(C$_1$-C$_4$ alkyl)$_q$NH$_2$, —(C$_1$-C$_4$ alkyl)$_q$CONH$_2$, —(C$_1$-C$_4$ alkyl)NHCONH$_2$, —(C$_1$-C$_4$ alkyl)NHCOH, —(C$_1$-C$_4$ alkyl)$_q$NHCOCH$_3$ or a group of formula (III):

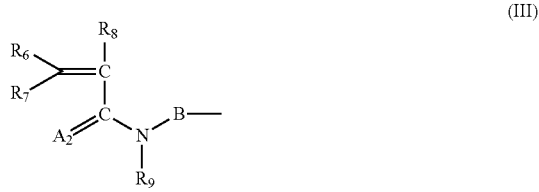

(III)

where B is —CH$_2$—, —CH$_2$—CH$_2$—, —CH$_2$—CH$_2$—CH$_2$—, —CH(CH$_3$)—CH$_2$— and —CH$_2$—CH(CH$_3$)—, and each q is 0 or 1; and
each $X_2$ is independently —H, —OH, —(C$_1$-C$_{10}$ alkyl), —(C$_1$-C$_{10}$ heteroalkyl), —(C$_3$-C$_8$ cycloalkyl), -(aryl), -(5- to 10-membered heteroaryl), —(C$_1$-C$_{10}$ alkyl)(aryl), -(aryl)(C$_1$-C$_{10}$ alkyl), —(C$_1$-C$_4$ alkyl)$_q$NH$_2$, —(C$_1$-C$_4$ alkyl)$_q$CONH$_2$, —(C$_1$-C$_4$ alkyl)NHCONH$_2$, —(C$_1$-C$_4$ alkyl)$_q$NHCOH or —(C$_1$-C$_4$ alkyl)$_q$NHCOCH$_3$, where each q is 0 or 1; or
mixtures thereof;
(f) provided that at least one of $A_1$ and $A_2$ is not O.

A polymer comprising at least one monomer of type $M_1$ and, optionally, one or more monomers of the type $M_2$, or a salt thereof (the polymer being a "polymer of the invention") is useful for separating a mixture of biomolecules using CE.

A second embodiment of the invention relates to a method for making a polymer of the invention, comprising the step of polymerizing at least one $M_1$ monomer, defined above, optionally in the presence of one or more monomers of type $M_2$, where $M_2$ is defined above. Thus; it is to be understood that a polymer of the invention can be a homopolymer or a copolymer.

A third embodiment of the invention relates to a composition comprising (a) a polymer of the invention and (b) a buffer (the composition being a "composition of the invention").

A fourth embodiment of the invention relates to a method for making a composition of the invention, comprising admixing (a) a polymer of the invention and (b) a buffer.

A fifth embodiment of the invention relates to a method for separating a mixture of biomolecules, comprising:
(a) contacting a composition of the invention with a mixture comprising a biomolecule; and
(b) applying an electric field to the composition in an amount sufficient to facilitate the separation of a biomolecule from the mixture.

A sixth embodiment of the invention relates to a capillary, e.g., a capillary tube, containing a composition of the invention.

These and other objects, features and advantages of the present invention will become better understood with reference to the following description, which illustrates non-limiting embodiments of the invention.

4. DETAILED DESCRIPTION OF THE INVENTION

The invention relates generally to a polymer of the invention, comprising an "N-vinylamide-type monomer," i.e., a monomer of formula (I); their preparation; compositions comprising the same; and uses thereof. The invention also relates to supports, such as capillaries, containing these polymers and methods for separating a mixture of biomolecules, especially polynucleotides, using CE.

As used herein, a "copolymer" is a polymer comprising two or more different monomeric subunits. Thus, a polymeric chain comprising three different monomers (also known as a terpolymer) is included within the term "copolymer," as is a polymer chain comprising more than three different monomeric units. As used herein, the term "polymer" includes a homopolymer and a copolymer. Accordingly, a polymer of the invention can be a homopolymer or a copolymer.

In polymers of the invention, x is an integer from 1 to 5 and y is an integer from 0 to 5. In some embodiments, x is 1. In some embodiments, y is 0. In some embodiments, y is an integer from 1 to 5. Additional embodiments are discussed elsewhere herein.

It is to be understood that a polymer of the invention can comprise: (a) monomers of a single monomer subtype, e.g., a polymer having the form poly($M_1^1M_2^0$) (or poly($M_1^1$)), that is, an $M_1$ homopolymer; (b) monomers selected from more than one subtype of $M_1$, e.g., a polymer having the form poly($M_1^2M_2^0$) (or poly($M_1^2$)) is an $M_1$ copolymer containing monomers of a first subtype of $M_1$ and also monomers of a second subtype of $M_1$; and (c) monomers of one or more monomer subtypes of type $M_1$ and monomers of one or more monomer subtypes of type $M_2$, e.g., a polymer having the form poly($M_1^2M_2^1$) contains two monomer subtypes of type $M_1$ and one monomer subtype of type $M_2$, that is, an $M_1/M_2$ copolymer.

Copolymers can be formed using many ways known to those skilled in the art, for example: by copolymerization of two or more different monomers, which copolymerization can be of the random type, the alternating type or intermediate between these two types, i.e., "intermediate-type"; by block copolymerization; by graft copolymerization, e.g., where an existing polymer chain is further reacted with a different monomer; and by a post-polymerization reaction, e.g., where a polymer's ester side groups are partially hydrolyzed. A copolymer is conventionally known as "random" or "ideal" when a radical formed from either monomer unit at the end of the growing polymer chain has about the same preference for adding either of the monomers and as "alternating" when a radical formed from one monomer at the end of the growing polymer chain prefers to add to the other monomer. See, e.g., F. W. Billmeyer, Jr., *Textbook of Polymer Science* 330-331 (Wiley-Interscience, New York, 2$^{nd}$ ed. 1971).

The IUPAC source-based nomenclature for copolymers uses the prefix "poly" followed by the names of the monomers connected by a term signifying the arrangement of the monomers. The connector "-co-" is commonly used and signifies a copolymer of the monomers where their arrangement is unspecified. See C. A. Costello and D. N. Schulz, *Copolymers in Kirk-Othmer Encyc. of Chem. Technol.* Vol. 7, 350 (4$^{th}$ ed. 1993). For example, poly(N-vinylamide-co-4-vinyl-morpholine) denotes a copolymer comprising N-vinylamide and 4-vinyl-morpholine monomer units and includes random-type, alternating-type and intermediate-type copolymers. Similarly, poly(N-vinylamide-co-vinyl acetate-co-N-butoxymethyl-methacrylamide) denotes a copolymer comprising N-vinylamide, vinyl acetate and N-butoxymethyl-methacrylamide monomer units and includes random-type, alternating-type and intermediate-type copolymers. Likewise, poly(N-vinylamide-co-N-methyl-N-vinylacetamide-co-N-butoxymethyl-methacrylamide) denotes a copolymer comprising N-vinylamide, N-methyl-N-vinylacetamide and N-butoxymethyl-methacrylamide monomer units and includes random-type, alternating-type and intermediate-type copolymers.

4.1. Polymers of the Invention

The first embodiment of the invention relates to a polymer of the invention having the form poly($M_1^x M_2^y$), or a salt thereof, comprising one or more monomers of type $M_1$ and optionally one or more monomers of type $M_2$, wherein:

(a) each monomer in the polymer is of type $M_1$ or $M_2$;
(b) x is an integer ranging from 1 to 5 and represents the number of monomer subtypes of type $M_1$ that are present in the polymer;
(c) y is an integer ranging from 0 to 5 and represents the number of monomer subtypes of type $M_2$ that are present in the polymer;
(d) each monomer subtype of type $M_1$ in the polymer independently has the formula (I):

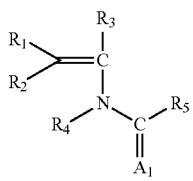

(I)

where each $A_1$ is independently =O, =S or =N$X_1$;
each of $R_1$, $R_2$, $R_3$ and $R_4$ is independently H, —($C_1$-$C_{10}$ alkyl), —($C_3$-$C_8$ cycloalkyl), -(aryl), -(5- to 10-membered heteroaryl), —($C_1$-$C_{10}$ alkyl)(aryl) or -(aryl)($C_1$-$C_{10}$ alkyl);
each $R_5$ is independently —(H), —($C_1$-$C_{10}$ alkyl), —($C_1$-$C_{10}$ heteroalkyl), —($C_3$-$C_8$ cycloalkyl), -(3- to 8-membered heterocycloalkyl), -(aryl), -(5- to 10-membered heteroaryl), —($C_1$-$C_{10}$ alkyl)($C_3$-$C_8$ cycloalkyl), —($C_3$-$C_8$ cycloalkyl)($C_1$-$C_{10}$ alkyl), —($C_1$-$C_{10}$ heteroalkyl)($C_3$-$C_8$ cycloalkyl), —($C_3$-$C_8$ cycloalkyl)($C_1$-$C_{10}$ heteroalkyl), —($C_1$-$C_{10}$ alkyl)(3- to 8-membered heterocycloalkyl), -(3- to 8-membered heterocycloalkyl)($C_1$-$C_{10}$ alkyl), —($C_1$-$C_{10}$ heteroalkyl)(3- to 8-membered heterocycloalkyl), -(3- to 8-membered heterocycloalkyl)($C_1$-$C_{10}$ heteroalkyl), —($C_1$-$C_{10}$ alkyl)(aryl), -(aryl)($C_1$-$C_{10}$ alkyl), —($C_1$-$C_{10}$ heteroalkyl)(aryl), -(aryl)($C_1$-$C_{10}$ heteroalkyl), —($C_1$-$C_{10}$ alkyl)(5- to 10-membered heteroaryl), -(5- to 10-membered heteroaryl)($C_1$-$C_{10}$ alkyl), —($C_1$-$C_{10}$ heteroalkyl)(5- to 10-membered heteroaryl), -(5- to 10-membered heteroaryl)($C_1$-$C_{10}$ heteroalkyl), —($C_1$-$C_4$ alkyl)$_p$NH$_2$, —($C_1$-$C_4$ alkyl)$_p$CONH$_2$, —($C_1$-$C_4$ alkyl)NHCONH$_2$, —($C_1$-$C_4$ alkyl)NHCOH or —($C_1$-$C_4$ alkyl)$_p$NHCOCH$_3$, where each p is 0 or 1; and each $X_1$ is independently —H, —($C_1$-$C_{10}$ alkyl), —($C_3$-$C_8$ cycloalkyl), -(aryl), -(5- to 10-membered heteroaryl), —($C_1$-$C_{10}$ alkyl)(aryl), -(aryl)($C_1$-$C_{10}$ alkyl), —($C_1$-$C_4$ alkyl)$_p$NH$_2$, —($C_1$-$C_4$ alkyl)$_p$CONH$_2$, —($C_1$-$C_4$ alkyl)NHCONH$_2$, —($C_1$-$C_4$ alkyl)$_p$NHCOH or —($C_1$-$C_4$ alkyl)$_p$NHCOCH$_3$, where each p is 0 or 1; and (e) when y is not zero, each monomer subtype of type $M_2$ in the polymer is independently:
1-vinyl-pyrrolidine-2,5-dione;
3-vinyl-oxazolidin-2-one;
1-vinyl-imidazolidin-2-one;
4-vinyl-morpholin-3,5-dione;
4-vinyl-morpholin-3-one;
4-vinyl-morpholine;
2-vinyl-1,3-dioxolane;
2-vinylene carbonate;
methoxyethylene;
vinyl acetate;
vinyl alcohol;
a monomer of formula (II):

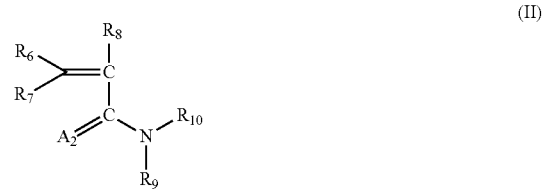

(II)

where each $A_2$ is independently =O, =S or =N$X_2$;
each of $R_6$, $R_7$, $R_8$ and $R_9$ is independently —H, —($C_1$-$C_{10}$ alkyl), —($C_3$-$C_8$ cycloalkyl), -(aryl), -(5- to 10-membered heteroaryl), —($C_1$-$C_{10}$ alkyl)(aryl) or -(aryl)($C_1$-$C_{10}$ alkyl);
each $R_{10}$ is independently —H, —OH, —($C_1$-$C_{10}$ alkyl), —($C_1$-$C_{10}$ heteroalkyl), —($C_3$-$C_8$ cycloalkyl), -(3- to 8-membered-heterocycloalkyl), -(aryl), -(5- to 10-membered heteroaryl), —($C_1$-$C_{10}$ alkyl)($C_3$-$C_8$ cycloalkyl), —($C_3$-$C_8$ cycloalkyl)($C_1$-$C_{10}$ alkyl), —($C_1$-$C_{10}$ heteroalkyl)($C_3$-$C_8$ cycloalkyl), —($C_3$-$C_8$ cycloalkyl)($C_1$-$C_{10}$ heteroalkyl), —($C_1$-$C_{10}$ alkyl)(3- to 8-membered heterocycloalkyl), -(3- to 8-membered heterocycloalkyl)($C_1$-$C_{10}$ alkyl), —($C_1$-$C_{10}$ heteroalkyl)(3- to 8-membered heterocycloalkyl), -(3- to 8-membered heterocycloalkyl)($C_1$-$C_{10}$ heteroalkyl), —($C_1$-$C_{10}$ alkyl)(aryl), -(aryl)($C_1$-$C_{10}$ alkyl), —($C_1$-$C_{10}$ heteroalkyl)(aryl), -(aryl)($C_1$-$C_{10}$ heteroalkyl), —($C_1$-$C_{10}$ alkyl)(5- to 10-membered heteroaryl), -(5- to 10-membered heteroaryl)($C_1$-$C_{10}$ alkyl), —($C_1$-$C_{10}$ heteroalkyl)(5- to 10-membered heteroaryl), -(5- to 10-membered heteroaryl)($C_1$-$C_{10}$ heteroalkyl), —($C_1$-$C_4$ alkyl)$_q$NH$_2$, —($C_1$-$C_4$ alkyl)$_q$CONH$_2$, —($C_1$-$C_4$ alkyl)NHCONH$_2$, —($C_1$-$C_4$ alkyl)NHCOH, —($C_1$-$C_4$ alkyl)$_q$NHCOCH$_3$ or a group of formula (III):

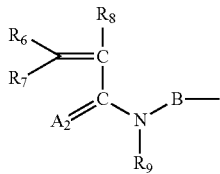

(III)

where B is —CH$_2$—, —CH$_2$—CH$_2$—, —CH$_2$—CH$_2$—CH$_2$—, —CH(CH$_3$)—CH$_2$— and —CH$_2$—CH(CH$_3$)—, and each q is 0 or 1; and each X$_2$ is independently —H, —OH, —($C_1$-$C_{10}$ alkyl), —($C_1$-$C_{10}$ heteroalkyl), —($C_3$-$C_8$ cycloalkyl), -(aryl), -(5- to 10-membered heteroaryl), —($C_1$-$C_{10}$ alkyl)(aryl), -(aryl)($C_1$-$C_{10}$ alkyl), —($C_1$-$C_4$ alkyl)$_q$NH$_2$, ($C_1$-$C_4$ alkyl)$_q$CONH$_2$, —($C_1$-$C_4$ alkyl)NHCONH$_2$, —($C_1$-$C_4$ alkyl)$_q$NHCOH or —($C_1$-$C_4$ alkyl)$_q$NHCOCH$_3$, where each q is 0 or 1; or mixtures thereof;

(f) provided that at least one of A$_1$ and A$_2$ is not O.

In certain embodiments, x is 1 and y is 0.
In certain embodiments, x is 2 and y is 0.
In certain embodiments, x is 3 and y is 0.
In certain embodiments, x is 4 and y is 0.
In certain embodiments, x is 5 and y is 0.
In certain embodiments, x is 1 and y is 1.
In certain embodiments, x is 2 and y is 1.
In certain embodiments, x is 3 and y is 1.
In certain embodiments, x is 4 and y is 1.
In certain embodiments, x is 5 and y is 1.
In certain embodiments, x is 1 and y is 2.
In certain embodiments, x is 2 and y is 2.
In certain embodiments, x is 3 and y is 2.
In certain embodiments, x is 4 and y is 2.
In certain embodiments, x is 5 and y is 2.
In certain embodiments, x is 1 and y is 3.
In certain embodiments, x is 2 and y is 3.
In certain embodiments, x is 3 and y is 3.
In certain embodiments, x is 4 and y is 3.
In certain embodiments, x is 5 and y is 3.
In certain embodiments, x is 1 and y is 4.
In certain embodiments, x is 2 and y is 4.
In certain embodiments, x is 3 and y is 4.
In certain embodiments, x is 4 and y is 4.
In certain embodiments, x is 5 and y is 4.
In certain embodiments, x is 1 and y is 5.
In certain embodiments, x is 2 and y is 5.
In certain embodiments, x is 3 and y is 5.
In certain embodiments, x is 4 and y is 5.
In certain embodiments, x is 5 and y is 5.

In certain embodiments, y is 0 and, for each monomer subtype of type M$_1$:
R$_1$ and R$_2$ are H; and
each R$_3$ is independently H or methyl.

In other embodiments y is 0 and, for each monomer subtype of type M$_1$:
R$_1$ and R$_2$ are H;
each R$_3$, R$_4$ and R$_5$ is independently H or methyl.

In another embodiment, y is 0 and, for each monomer subtype of type M$_1$:
R$_1$, R$_2$, R$_3$, R$_4$ and R$_5$ are H.

In another embodiment, y is 0 and, for each monomer subtype of type M$_1$:
R$_1$, R$_2$, R$_3$, and R$_4$ are H; and
R$_5$ is methyl.

In another embodiment, y is 0 and, for each monomer subtype of type M$_1$:
R$_1$, R$_2$ and R$_3$ are H; and
R$_4$ and R$_5$ are methyl.

In certain embodiments, y is 0, x is 2 and, for each monomer subtype of type M$_1$:
R$_1$ and R$_2$ are H; and
each R$_3$ is independently H or methyl.

In other embodiments, y is 0, x is 2 and, for each monomer subtype of type M$_1$:
R$_1$ and R$_2$ are H;
each R$_3$, R$_4$ and R$_5$ is independently H or methyl.

In another embodiment, y is 0, x is 2 and, for each monomer subtype of type M$_1$:
R$_1$, R$_2$, R$_3$, R$_4$ and R$_5$ are H.

In another embodiment, y is 0, x is 2 and, for each monomer subtype of type M$_1$:
R$_1$, R$_2$, R$_3$, and R$_4$ are H; and
R$_5$ is methyl.

In another embodiment, y is 0, x is 2 and, for each monomer subtype of type M$_1$:
R$_1$, R$_2$ and R$_3$ are H; and
R$_4$ and R$_5$ are methyl.

In certain embodiments, y is 0, x is 1 and, for M$_1$:
R$_1$ and R$_2$ are H; and
each R$_3$ is independently H or methyl.

In other embodiments, y is 0, x is 1 and, for M$_1$:
R$_1$ and R$_2$ are H;
each R$_3$, R$_4$ and R$_5$ is independently H or methyl.

In another embodiment, y is 0, x is 1 and, for M$_1$:
R$_1$, R$_2$, R$_3$, R$_4$ and R$_5$ are H.

In another embodiment, y is 0, x is 1 and, for M$_1$:
R$_1$, R$_2$, R$_3$, and R$_4$ are H; and
R$_5$ is methyl.

In another embodiment, y is 0, x is 1 and, for M$_1$:
R$_1$, R$_2$ and R$_3$ are H; and
R$_4$ and R$_5$ are methyl.

In certain embodiments:
(a) for each monomer subtype of type M$_1$:
A$_1$ is O;
R$_1$ and R$_2$ are H; and
each R$_3$ is independently H or methyl;
(b) y is 2; and
(c) for each monomer subtype of type M$_2$ of formula (II):
R$_6$ and R$_7$ are H; and
each R$_8$ is independently H or methyl.

In certain embodiments:
(a) for each monomer subtype of type M$_1$:
A$_1$ is O;
R$_1$ and R$_2$ are H; and
each R$_3$ is independently H or methyl;
(b) y is 1; and
(c) for M$_2$ of formula (II):
R$_6$ and R$_7$ are H; and
each R$_8$ is independently H or methyl.

In certain embodiments:
(a) x is 2;
(b) for each monomer subtype of type M$_1$:
A$_1$ is O;
R$_1$ and R$_2$ are H; and
each R$_3$ is independently H or methyl;

(c) y is 2; and
(d) for each monomer subtype of type $M_2$ of formula (II):
$R_6$ and $R_7$ are H; and
each $R_8$ is independently H or methyl.
In certain embodiments:
(a) x is 2;
(b) for each monomer subtype of type $M_1$:
$A_1$ is O;
$R_1$ and $R_2$ are H; and
each $R_3$ is independently H or methyl;
(c) y is 1; and
(d) for $M_2$ of formula (II):
$R_6$ and $R_7$ are H; and
each $R_8$ is independently H or methyl.
In certain embodiments:
(a) x is 1;
(b) for $M_1$:
$A_1$ is O;
$R_1$ and $R_2$ are H; and
each $R_3$ is independently H or methyl;
(c) y is 2; and
(d) for each monomer subtype of type $M_2$ of formula (II):
$R_6$ and $R_7$ are H; and
each $R_8$ is independently H or methyl.
In certain embodiments:
(a) x is 1;
(b) for $M_1$:
$A_1$ is O;
$R_1$ and $R_2$ are H; and
each $R_3$ is independently H or methyl;
(c) y is 1; and
(d) for $M_2$ of formula (II):
$R_6$ and $R_7$ are H; and
each $R_8$ is independently H or methyl.

In some embodiments, $M_1$, or each monomer subtype of type $M_1$ if x>1, is N-vinylformamide, N-vinylacetamide, N-vinylpropamide, N-vinylbutamide, N-vinylpentamide, N-vinylhexamide, N-vinylheptamide, N-vinyloctamide, N-vinylnonamide, N-vinyldecamide, N-methyl-N-vinylformamide, N-methyl-N-vinylacetamide, N-methyl-N-vinylpropamide, N-methyl-N-vinylbutamide, N-methyl-N-vinylpentamide, N-methyl-N-vinylhexamide, N-methyl-N-vinylheptamide, N-methyl-N-vinyloctamide, N-methyl-N-vinylnonamide, N-methyl-N-vinyldecamide, N-ethyl-N-vinylformamide, N-ethyl-N-vinylacetamide, N-ethyl-N-vinylpropamide, N-ethyl-N-vinylbutamide, N-ethyl-N-vinylpentamide, N-ethyl-N-vinylhexamide, N-ethyl-N-vinylheptamide, N-ethyl-N-vinyloctamide, N-ethyl-N-vinylnonamide, N-ethyl-N-vinyldecamide, N-n-propyl-N-vinylformamide, N-n-propyl-N-vinylacetamide, N-n-propyl-N-vinylpropamide, N-n-propyl-N-vinylbutamide, N-n-propyl-N-vinylpentamide, N-n-propyl-N-vinylhexamide, N-n-propyl-N-vinylheptamide, N-n-propyl-N-vinyloctamide, N-n-propyl-N-vinylnonamide, N-n-propyl-N-vinyldecamide, N-iso-propyl-N-vinylformamide, N-iso-propyl-N-vinylacetamide, N-iso-propyl-N-vinylpropamide, N-iso-propyl-N-vinylbutamide, N-iso-propyl-N-vinylpentamide, N-iso-propyl-N-vinylhexamide, N-iso-propyl-N-vinylheptamide, N-iso-propyl-N-vinyloctamide, N-iso-propyl-N-vinylnonamide, N-iso-propyl-N-vinyldecamide, or a mixture thereof.

In some embodiments, $M_1$, or each monomer subtype of type $M_1$ if x>1, is N-vinylformamide, N-vinylacetamide, N-vinylpropamide, N-vinylbutamide, N-methyl-N-vinylformamide, N-methyl-N-vinylacetamide, N-methyl-N-vinylpropamide, N-methyl-N-vinylbutamide, N-ethyl-N-vinylformamide, N-ethyl-N-vinylacetamide, N-ethyl-N-vinylpropamide, N-ethyl-N-vinylbutamide, N-n-propyl-N-vinylformamide, N-n-propyl-N-vinylacetamide, N-n-propyl-N-vinylpropamide, N-n-propyl-N-vinylbutamide, N-iso-propyl-N-vinylformamide, N-iso-propyl-N-vinylacetamide, N-iso-propyl-N-vinylpropamide, N-iso-propyl-N-vinylbutamide, or a mixture thereof.

In other embodiments, $M_2$, or each monomer subtype of type $M_2$ if y>1, is N-hydroxy-acrylamide, N-methoxy-acrylamide, acryloyl urea, 1-vinyl-pyrrolidine-2,5-dione, 3-vinyl-oxazolidin-2-one, 1-vinyl-imidazolidin-2-one, 4-vinyl-morpholin-3,5-dione, 4-vinyl-morpholin-3-one, 4-vinyl-morpholine, 2-vinyl-1,3-dioxolane, 2-vinylene carbonate, methoxyethylene, vinyl acetate, vinyl alcohol, or a mixture thereof.

It is conventional to prepare polymers or copolymers containing vinyl alcohol monomer units using indirect methods. For example, polymers containing vinyl alcohol monomer units can be prepared by performing at least a partial alcoholysis of poly(vinyl acetate), e.g., by using methanol or ethanol with an acid or base catalyst. See, e.g., F. W. Billmeyer, Jr., *Textbook of Polymer Science*, 416 ($2^{nd}$ ed. 1971). The alcoholysis is carried out conventionally, e.g., by dissolving or suspending poly(vinyl acetate) in the alcohol selected, adding the catalyst, and optionally heating.

In other embodiments, $M_2$, or each monomer subtype of type $M_2$ if y>1, is acrylamide, N-acetamido-acrylamide, N-acetyl-acrylamide, N-allyl-acrylamide, N-2-aminoethyl-acrylamide hydrochloride, N-2-aminoethyl-N-methyl-acrylamide hydrochloride, N-3-aminopropyl-acrylamide hydrochloride, N-3-aminopropyl-N-methyl-acrylamide hydrochloride, N-butoxymethyl-acrylamide, N-n-butyl-acrylamide, N-tert-butyl-acrylamide, N-2-cyanoethyl-acrylamide, N-cyanomethyl-acrylamide, N-cyanomethyl-N-methyl-acrylamide, N,N-diallyl-acrylamide, N,N-diethyl-acrylamide, N,N-diisopropyl-acrylamide, N,N-dimethyl-acrylamide, N,N'-ethylene-bis-acrylamide, N-ethyl-N-methyl-acrylamide, N-ethyl-N-propyl-acrylamide, N-2-glycolic acid-acrylamide, N-2-glycolic acid methyl ester-acrylamide, N-2-hydroxyethyl-acrylamide, N-2-hydroxyethyl-N-methyl-acrylamide, N-hydroxymethyl-acrylamide, N-hydroxymethyl-N-methyl-acrylamide, N-iso-propyl-acrylamide, N,N'-iso-propylene-bis-acrylamide, N-2-methoxyethyl-acrylamide, N-methoxymethyl-acrylamide, N-methyl-acrylamide, N,N'-methylene-bis-acrylamide, N-2,2,2-trichloro-1-hydroxyethyl-acrylamide, N-tri(hydroxymethyl)methyl-acrylamide, N-tri(hydroxymethyl)methyl-N-methyl-acrylamide, N, N'-trimethylene-bis-acrylamide, N-3-(trimethylammonium)propyl-acrylamide hydrochloride, N-3-(trimethylammonium)propyl-N-methyl-acrylamide hydrochloride, or a mixture thereof.

In embodiments where for $M_2$, $R_{10}$ is a group of formula (III), such as in the monomer unit N,N'-trimethylene-bis-acrylamide, the group B in formula (III) is methylene, ethylene, trimethylene and isopropylene. In this context, for the purposes of this application, "methylene" signifies the B group —$CH_2$—, "ethylene" signifies the B group —$CH_2$—$CH_2$—, "trimethylene" signifies the B group —$CH_2$—$CH_2$—$CH_2$—, and "isopropylene" signifies the B groups —$CH(CH_3)$—$CH_2$— and —$CH_2$—$CH(CH_3)$—.

In other embodiments, $M_2$, or each monomer subtype of type $M_2$ if y>1, is acrylamide, N-acetamido-acrylamide, N-acetyl-acrylamide, N-allyl-acrylamide, N-2-aminoethyl-acrylamide hydrochloride, N-2-aminoethyl-N-methyl-acrylamide hydrochloride, N-3-aminopropyl-acrylamide hydrochloride, N-3-aminopropyl-N-methyl-acrylamide hydrochloride, N-butoxymethyl-acrylamide, N-n-butyl-acrylamide, N-tert-butyl-acrylamide, N-2-cyanoethyl-acrylamide, N-cyanomethyl-acrylamide, N-cyanomethyl-N-methyl-acrylamide, N,N-diallyl-acrylamide, N,N-diethyl-acrylamide, N,N-diisopropyl-acrylamide, N,N-dimethyl-acrylamide, N-ethyl-N-methyl-acrylamide, N-ethyl-N-propyl-acrylamide, N-2-glycolic acid-acrylamide, N-2-glycolic acid methyl ester-acrylamide, N-2-hydroxyethyl-acrylamide, N-2-hydroxyethyl-N-methyl-acrylamide, N-hydroxymethyl-acrylamide, N-hydroxymethyl-N-methyl-acrylamide, N-iso-propyl-acrylamide, N-2-methoxyethyl-acrylamide, N-methoxymethyl-acrylamide, N-methyl-acrylamide, N-2,2,2-trichloro-1-hydroxyethyl-acrylamide, N-tri(hydroxymethyl)methyl-acrylamide, N-tri(hydroxymethyl)methyl-N-methyl-acrylamide, N-3-(trimethylammonium)propyl-acrylamide hydrochloride, N-3-(trimethylammonium)propyl-N-methyl-acrylamide hydrochloride, or a mixture thereof.

In other embodiments, $M_2$, or each monomer subtype of type $M_2$ if y>1, is methacrylamide, N-acetamido-methacrylamide, N-acetyl-methacrylamide, N-allyl-methacrylamide, N-2-aminoethyl-methacrylamide hydrochloride, N-3-aminopropyl-methacrylamide hydrochloride, N-butoxyethyl-methacrylamide, N-n-butyl-methacrylamide, N-tert-butyl-methacrylamide, N-2-cyanoethyl-methacrylamide, N-cyanomethyl-methacrylamide, N-cyanomethyl-N-methyl-methacrylamide, N,N-diethyl-methacrylamide, N,N-dimethyl-methacrylamide, N-2-glycolic acid-methacrylamide, N-2-hydroxyethyl-methacrylamide, N-hydroxymethyl-methacrylamide, N-hydroxymethyl-N-methyl-methacrylamide, N-iso-propyl-methacrylamide, N,N'-iso-propylene-bis-methacrylamide, N-2-methoxyethyl-methacrylamide, N-methoxymethyl-methacrylamide, N-methyl-methacrylamide, N,N'-methylene-bis-methacrylamide, N-tri(hydroxymethyl)methyl-methacrylamide, N,N'-trimethylene-bis-methacrylamide, N-3-(trimethylammonium)propyl-methacrylamide hydrochloride, or a mixture thereof.

In other embodiments, $M_2$, or each monomer subtype of type $M_2$ if y>1, is methacrylamide, N-acetamido-methacrylamide, N-acetyl-methacrylamide, N-allyl-methacrylamide, N-2-aminoethyl-methacrylamide hydrochloride, N-3-aminopropyl-methacrylamide hydrochloride, N-butoxyethyl-methacrylamide, N-n-butyl-methacrylamide, N-tert-butyl-methacrylamide, N-2-cyanoethyl-methacrylamide, N-cyanomethyl-methacrylamide, N-cyanomethyl-N-methyl-methacrylamide, N,N-diethyl-methacrylamide, N,N-dimethyl-methacrylamide, N-2-glycolic acid-methacrylamide, N-2-hydroxyethyl-methacrylamide, N-hydroxymethyl-methacrylamide, N-hydroxymethyl-N-methyl-methacrylamide, N-iso-propyl-methacrylamide, N-2-methoxyethyl-methacrylamide, N-methoxymethyl-methacrylamide, N-methyl-methacrylamide, N-tri(hydroxymethyl)methyl-methacrylamide, N-3-(trimethylammonium)propyl-methacrylamide hydrochloride, or a mixture thereof.

In other embodiments, $M_2$, or each monomer subtype of type $M_2$ if y>1, is acrylamide, N-acetamido-acrylamide, N-acetyl-acrylamide, N-allyl-acrylamide, N-2-aminoethyl-acrylamide hydrochloride, N-2-aminoethyl-N-methyl-acrylamide hydrochloride, N-3-aminopropyl-acrylamide hydrochloride, N-3-aminopropyl-N-methyl-acrylamide hydrochloride, N-butoxymethyl-acrylamide, N-n-butyl-acrylamide, N-tert-butyl-acrylamide, N-2-cyanoethyl-acrylamide, N-cyanomethyl-acrylamide, N-cyanomethyl-N-methyl-acrylamide, N,N-diallyl-acrylamide, N,N-diethyl-acrylamide, N,N-diisopropyl-acrylamide, N,N-dimethyl-acrylamide, N-ethyl-N-methyl-acrylamide, N-ethyl-N-propyl-acrylamide, N-2-glycolic acid-acrylamide, N-2-glycolic acid methyl ester-acrylamide, N-2-hydroxyethyl-acrylamide, N-2-hydroxyethyl-N-methyl-acrylamide, N-hydroxymethyl-acrylamide, N-hydroxymethyl-N-methyl-acrylamide, N-iso-propyl-acrylamide, N-2-methoxyethyl-acrylamide, N-methoxymethyl-acrylamide, N-methyl-acrylamide, N-2,2,2-trichloro-1-hydroxyethyl-acrylamide, N-tri(hydroxymethyl)methyl-acrylamide, N-tri(hydroxymethyl)methyl-N-methyl-acrylamide, N-3-(trimethylammonium)propyl-acrylamide hydrochloride, N-3-(trimethylammonium)propyl-N-methyl-acrylamide hydrochloride, methacrylamide, N-acetamido-methacrylamide, N-acetyl-methacrylamide, N-allyl-methacrylamide, N-2-aminoethyl-methacrylamide hydrochloride, N-3-aminopropyl-methacrylamide hydrochloride, N-butoxyethyl-methacrylamide, N-n-butyl-methacrylamide, N-tert-butyl-methacrylamide, N-2-cyanoethyl-methacrylamide, N-cyanomethyl-methacrylamide, N-cyanomethyl-N-methyl-methacrylamide, N,N-diethyl-methacrylamide, N,N-dimethyl-methacrylamide, N-2-glycolic acid-methacrylamide, N-2-hydroxyethyl-methacrylamide, N-hydroxymethyl-methacrylamide, N-hydroxymethyl-N-methyl-methacrylamide, N-iso-propyl-methacrylamide, N-2-methoxyethyl-methacrylamide, N-methoxymethylmethacrylamide, N-methyl-methacrylamide, N-tri(hydroxymethyl)methyl-methacrylamide, N-3-(trimethylammonium)propyl-methacrylamide hydrochloride, or a mixture thereof.

In other embodiments, $M_2$, or each monomer subtype of type $M_2$ if y>1, is N-acetamido-acrylamide, N-acetyl-acrylamide, N-allyl-acrylamide, N-2-aminoethyl-acrylamide hydrochloride, N-2-aminoethyl-N-methyl-acrylamide hydrochloride, N-3-aminopropyl-acrylamide hydrochloride, N-3-aminopropyl-N-methyl-acrylamide hydrochloride, N-butoxymethyl-acrylamide, N-n-butyl-acrylamide, N-2-cyanoethyl-acrylamide, N-cyanomethyl-acrylamide, N-cyanomethyl-N-methyl-acrylamide, N,N-diallyl-acrylamide, N,N-diisopropyl-acrylamide, N-ethyl-N-methyl-acrylamide, N-ethyl-N-propyl-acrylamide, N-2-glycolic acid-acrylamide, N-2-glycolic acid methyl ester-acrylamide, N-2-hydroxyethyl-acrylamide, N-2-hydroxyethyl-N-methyl-acrylamide, N-hydroxymethyl-acrylamide, N-hydroxymethyl-N-methyl-acrylamide, N-2-methoxyethyl-acrylamide, N-methoxymethyl-acrylamide, N-2,2,2-trichloro-1-hydroxyethyl-acrylamide, N-tri(hydroxymethyl)methyl-acrylamide, N-tri(hydroxymethyl)methyl-N-methyl-acrylamide, N-3-(trimethylammonium)propyl-acrylamide hydrochloride, N-3-(trimethylammonium)propyl-N-methyl-acrylamide hydrochloride, N-acetamido-methacrylamide, N-acetyl-methacrylamide, N-allyl-methacrylamide, N-2-aminoethyl-methacrylamide hydrochloride, N-3-aminopropyl-methacrylamide hydrochloride, N-butoxymethyl-methacrylamide, N-n-butyl-methacrylamide, N-tert-butyl-methacrylamide, N-2-cyanoethyl-methacrylamide, N-cyanomethyl-methacrylamide, N-cyanomethyl-N-methyl-methacrylamide, N,N-diethyl-methacrylamide, N,N-dimethyl-methacrylamide, N-2-glycolic acid-methacrylamide, N-2-hydroxyethyl-methacrylamide, N-hydroxymethyl-methacrylamide, N-hydroxymethyl-N-methyl-methacrylamide, N-iso-propyl-methacrylamide, N-2-methoxethyl-methacrylamide, N-methoxymethyl-methacrylamide, N-methyl-methacrylamide, N-tri(hydroxymethyl)methyl-methacrylamide, N-3-(trimethylammonium)propyl-methacrylamide hydrochloride, or a mixture thereof.

In other embodiments, $M_2$, or each monomer subtype of type $M_2$ if y>1, is N-hydroxy-acrylamide, N-methoxy-acrylamide, acryloyl urea, 1-vinyl-pyrrolidine-2,5-dione, 3-vinyl-oxazolidin-2-one, 1-vinyl-imidazolidin-2-one, 4-vinyl-morpholin-3,5-dione, 4-vinyl-morpholin-3-one, 4-vinyl-morpholine, 2-vinyl-1,3-dioxolane, 2-vinylene carbonate, methoxyethylene, vinyl acetate, vinyl alcohol, acrylamide, N-acetamido-acrylamide, N-acetyl-acrylamide, N-allyl-acrylamide, N-2-aminoethyl-acrylamide hydrochloride, N-2-aminoethyl-N-methyl-acrylamide hydrochloride, N-3-aminopropyl-acrylamide hydrochloride, N-3-aminopropyl-N-methyl-acrylamide hydrochloride, N-butoxymethyl-acrylamide, N-n-butyl-acrylamide, N-tert-butyl-acrylamide, N-2-cyanoethyl-acrylamide, N-cyanomethyl-acrylamide, N-cyanomethyl-N-methyl-acrylamide, N,N-diallyl-acrylamide, N,N-diethyl-acrylamide, N,N-diisopropyl-acrylamide, N,N-dimethyl-acrylamide, N,N'-ethylene-bis-acrylamide, N-ethyl-N-methyl-acrylamide, N-ethyl-N-propyl-acrylamide, N-2-glycolic acid-acrylamide, N-2-glycolic acid methyl ester-acrylamide, N-2-hydroxyethyl-acrylamide, N-2-hydroxyethyl-N-methyl-acrylamide, N-hydroxymethyl-acrylamide, N-hydroxymethyl-N-methyl-acrylamide, N-iso-propyl-acrylamide, N,N'-iso-propylene-bis-acrylamide, N-2-methoxyethyl-acrylamide, N-methoxymethyl-acrylamide, N-methyl-acrylamide, N,N'-methylene-bis-acrylamide, N-2,2,2-trichloro-1-hydroxyethyl-acrylamide, N-tri(hydroxymethyl)methyl-acrylamide, N-tri(hydroxymethyl)methyl-N-methyl-acrylamide, N,N'-trimethylene-bis-acrylamide, N-3-(trimethylammonium)propyl-acrylamide hydrochloride, N-3-(trimethylammonium)propyl-N-methyl-acrylamide hydrochloride, methacrylamide, N-acetamido-methacrylamide, N-acetyl-methacrylamide, N-allyl-methacrylamide, N-2-aminoethyl-methacrylamide hydrochloride, N-3-aminopropyl-methacrylamide hydrochloride, N-butoxymethyl-methacrylamide, N-n-butyl-methacrylamide, N-tert-butyl-methacrylamide, N-2-cyanoethyl-methacrylamide, N-cyanomethyl-methacrylamide, N-cyanomethyl-N-methyl-methacrylamide, N,N-diethyl-methacrylamide, N,N-dimethyl-methacrylamide, N-2-glycolic acid-methacrylamide, N-2-hydroxyethyl-methacrylamide, N-hydroxymethyl-methacrylamide, N-hydroxymethyl-N-methyl-methacrylamide, N-iso-propyl-methacrylamide, N,N'-iso-propylene-bis-methacrylamide, N-2-methoxethyl-methacrylamide, N-methoxymethyl-methacrylamide, N-methyl-methacrylamide, N,N'-methylene-bis-methacrylamide, N-tri(hydroxymethyl)methyl-methacrylamide, N,N'-trimethylene-bis-methacrylamide, N-3-(trimethylammonium)propyl-methacrylamide hydrochloride, or a mixture thereof.

In other embodiments, $M_2$, or each monomer subtype of type $M_2$ if y>1, is N-hydroxy-acrylamide, N-methoxy-acrylamide, acryloyl urea, 1-vinyl-pyrrolidine-2,5-dione, 3-vinyl-oxazolidin-2-one, 1-vinyl-imidazolidin-2-one, 4-vinyl-morpholin-3,5-dione, 4-vinyl-morpholin-3-one, 4-vinyl-morpholine, 2-vinyl-1,3-dioxolane, 2-vinylene carbonate, methoxyethylene, vinyl acetate, vinyl alcohol, acrylamide, N-acetamido-acrylamide, N-acetyl-acrylamide, N-allyl-acrylamide, N-2-aminoethyl-acrylamide hydrochloride, N-2-aminoethyl-N-methyl-acrylamide hydrochloride, N-3-aminopropyl-acrylamide hydrochloride, N-3-aminopropyl-N-methyl-acrylamide hydrochloride, N-butoxymethyl-acrylamide, N-n-butyl-acrylamide, N-tert-butyl-acrylamide, N-2-cyanoethyl-acrylamide, N-cyanomethyl-acrylamide, N-cyanomethyl-N-methyl-acrylamide, N,N-diallyl-acrylamide, N,N-diethyl-acrylamide, N,N-diisopropyl-acrylamide, N,N-dimethyl-acrylamide, N-ethyl-N-methyl-acrylamide, N-ethyl-N-propyl-acrylamide, N-2-glycolic acid-acrylamide, N-2-glycolic acid methyl ester-acrylamide, N-2-hydroxyethyl-acrylamide, N-2-hydroxyethyl-N-methyl-acrylamide, N-hydroxymethyl-acrylamide, N-hydroxymethyl-N-methyl-acrylamide, N-iso-propyl-acrylamide, N-2-methoxyethyl-acrylamide, N-methoxymethyl-acrylamide, N-methyl-acrylamide, N-2,2,2-trichloro-1-hydroxyethyl-acrylamide, N-tri(hydroxymethyl)methyl-acrylamide, N-tri(hydroxymethyl)methyl-N-methyl-acrylamide, N-3-(trimethylammonium)propyl-acrylamide hydrochloride, N-3-(trimethylammonium)propyl-N-methyl-acrylamide hydrochloride, methacrylamide, N-acetamido-methacrylamide, N-acetyl-methacrylamide, N-allyl-methacrylamide, N-2-aminoethyl-methacrylamide hydrochloride, N-3-aminopropyl-methacrylamide hydrochloride, N-butoxymethyl-methacrylamide, N-n-butyl-methacrylamide, N-tert-butyl-methacrylamide, N-2-cyanoethyl-methacrylamide, N-cyanomethyl-methacrylamide, N-cyanomethyl-N-methyl-methacrylamide, N,N-diethyl-methacrylamide, N,N-dimethyl-methacrylamide, N-2-glycolic acid-methacrylamide, N-2-hydroxyethyl-methacrylamide, N-hydroxymethyl-methacrylamide, N-hydroxymethyl-N-methyl-methacrylamide, N-iso-propyl-methacrylamide, N-2-methoxyethyl-methacrylamide, N-methoxymethyl-methacrylamide, N-methyl-methacrylamide, N-tri(hydroxymethyl)methyl-methacrylamide, N-3-(trimethylammonium)propyl-methacrylamide hydrochloride, or a mixture thereof.

In other embodiments, $M_2$, or each monomer subtype of type $M_2$ if y>1, is N-hydroxy-acrylamide, N-methoxy-acrylamide, acryloyl urea, 1-vinyl-pyrrolidine-2,5-dione, 3-vinyl-oxazolidin-2-one, 1-vinyl-imidazolidin-2-one, 4-vinyl-morpholin-3,5-dione, 4-vinyl-morpholin-3-one, 4-vinyl-morpholine, 2-vinylene carbonate, methoxyethylene, N-acetamido-acrylamide, N-acetyl-acrylamide, N-allyl-acrylamide, N-2-aminoethyl-acrylamide hydrochloride, N-2-aminoethyl-N-methyl-acrylamide hydrochloride, N-3-aminopropyl-acrylamide hydrochloride, N-3-aminopropyl-N-methyl-acrylamide hydrochloride, N-butoxymethyl-acrylamide, N-n-butyl-acrylamide, N-2-cyanoethyl-acrylamide, N-cyanomethyl-acrylamide, N-cyanomethyl-N-methyl-acrylamide, N,N-diallyl-acrylamide, N,N-diisopropyl-acrylamide, N-ethyl-N-methyl-acrylamide, N-ethyl-N-propyl-acrylamide, N-2-glycolic acid-acrylamide, N-2-glycolic acid methyl ester-acrylamide, N-2-hydroxyethyl-acrylamide, N-2-hydroxyethyl-N-methyl-acrylamide, N-hydroxyethyl-acrylamide, N-hydroxymethyl-N-methyl-acrylamide, N-2-methoxyethyl-acrylamide, N-methoxymethyl-acrylamide, N-2,2,2-trichloro-1-hydroxyethyl-acrylamide, N-tri(hydroxymethyl)methyl-acrylamide, N-tri(hydroxymethyl)methyl-N-methyl-acrylamide, N-3-(trimethylammonium)propyl-acrylamide hydrochloride, N-3-(trimethylammonium)propyl-N-methyl-acrylamide hydrochloride, N-acetamido-methacrylamide, N-acetyl-methacrylamide, N-allyl-methacrylamide, N-2-aminoethyl-methacrylamide hydrochloride, N-3-aminopropyl-methacrylamide hydrochloride, N-butoxymethyl-methacrylamide, N-n-butyl-methacrylamide, N-tert-butyl-methacrylamide, N-2-cyanoethyl-methacrylamide, N-cyanomethyl-methacrylamide, N-cyanomethyl-N-methyl-methacrylamide, N,N-diethyl-methacrylamide, N,N-dimethyl-methacrylamide, N-2-glycolic acid-methacrylamide, N-2-hydroxyethyl-methacrylamide, N-hydroxymethyl-methacrylamide, N-hydroxymethyl-N-methyl-methacrylamide, N-iso-propyl-methacrylamide, N-2-methoxyethyl-methacrylamide, N-methoxymethyl-methacrylamide, N-methyl-methacrylamide, N-tri(hydroxymethyl)methyl-methacrylamide, N-3-(trimethylammonium)propyl-methacrylamide hydrochloride, or a mixture thereof.

In other embodiments, in each of the preceding embodiments for $M_2$, each $M_1$, or each monomer subtype of type $M_1$ if x>1, is independently N-vinylformamide, N-vinylacetamide or N-methyl-N-vinylacetamide or, alternatively, each $M_1$, or each monomer subtype of type $M_1$ if x>1, is independently N-vinylformamide or N-methyl-N-vinylacetamide.

In other embodiments, the polymer of the invention is a copolymer that is poly(N-vinylformamide-co-N-methyl-acrylamide); poly(N-vinylformamide-co-N,N-diethyl-acrylamide); poly(N-vinylformamide-co-N-methoxymethyl-acrylamide); poly(N-vinylformamide-co-N-methoxy-acrylamide); poly(N-vinylformamide-co-N-2-hydroxyethyl-acrylamide); poly(N-vinylformamide-co-N-methyl-methacrylamide); poly(N-vinylformamide-co-N,N-dimethyl-methacrylamide); poly(N-vinylformamide-co-N-methoxymethyl-methacrylamide); poly(N-vinylformamide-co-N-2-hydroxyethyl-methacrylamide); poly(N-vinylformamide-co-1-vinyl-pyrrolidine-2,5-dione); poly(N-vinylformamide-co-2-vinylene carbonate); poly(N-vinylformamide-co-vinyl acetate-co-2-vinylene carbonate); poly(N-vinylacetamide-co-N-methoxymethyl-acrylamide); poly(N-vinylacetamide-co-N-methoxy-acrylamide); poly(N-vinylacetamide-co-N-2-hydroxyethyl-acrylamide); poly(N-vinylacetamide-co-methacrylamide); poly(N-vinylacetamide-co-N-methyl-methacrylamide); poly(N-vinylacetamide-co-N-methoxymethyl-methacrylamide); poly(N-vinylacetamide-co-N-2-hydroxyethyl-methacrylamide); poly(N-vinylacetamide-co-1-vinyl-pyrrolidine-2,5-dione); poly(N-vinylacetamide-co-2-vinylene carbonate); poly(N-vinylacetamide-co-vinyl acetate-co-2-vinylene carbonate); poly(N-methyl-N-vinylacetamide-co-N-methyl-acrylamide); poly(N-methyl-N-vinylacetamide-co-N,N-diethyl-acrylamide); poly(N-methyl-N-vinylacetamide-co-N-methoxymethyl-acrylamide); poly(N-methyl-N-vinylacetamide-co-N-methoxy-acrylamide); poly(N-methyl-N-vinylacetamide-co-N-2-hydroxyethyl-acrylamide); poly(N-methyl-N-vinylacetamide-co-N-methyl-methacrylamide); poly(N-methyl-N-vinylacetamide-co-N,N-dimethyl-methacrylamide); poly(N-methyl-N-vinylacetamide-co-N-methoxymethyl-methacrylamide); poly(N-methyl-N-vinylacetamide-co-N-2-hydroxyethyl-methacrylamide); poly(N-methyl-N-vinylacetamide-co-1-vinyl-pyrrolidine-2,5-dione); poly(N-methyl-N-vinylacetamide-co-2-vinylene carbonate); poly(N-methyl-N-vinylacetamide-co-vinyl acetate-co-2-vinylene carbonate); or salts thereof.

In other embodiments, the polymer of the invention is a copolymer that is poly(N-vinylformamide-co-N-methoxymethyl-acrylamide); poly(N-vinylformamide-co-N-methoxy-acrylamide); poly(N-vinylformamide-co-N-2-hydroxyethyl-acrylamide); poly(N-vinylformamide-co-N-methyl-methacrylamide); poly(N-vinylformamide-co-N-methoxymethyl-methacrylamide); poly(N-vinylformamide-co-N-2-hydroxyethyl-methacrylamide); poly(N-vinylformamide-co-1-vinyl-pyrrolidine-2,5-dione); poly(N-vinylformamide-co-2-vinylene carbonate); poly(N-vinylacetamide-co-N-methoxymethyl-acrylamide); poly(N-vinylacetamide-co-N-methoxy-acrylamide); poly(N-vinylacetamide-co-N-2-hydroxyethyl-acrylamide); poly(N-vinylacetamide-co-N-methyl-methacrylamide); poly(N-vinylacetamide-co-N-methoxymethyl-methacrylamide); poly(N-vinylacetamide-co-N-2-hydroxyethyl-methacrylamide); poly(N-vinylacetamide-co-1-vinyl-pyrrolidine-2,5-dione); poly(N-vinylacetamide-co-2-vinylene carbonate); poly(N-methyl-N-vinylacetamide-co-N-methoxymethyl-acrylamide); poly(N-methyl-N-vinylacetamide-co-N-methoxy-acrylamide); poly(N-methyl-N-vinylacetamide-co-N-2-hydroxyethyl-acrylamide); poly(N-methyl-N-vinylacetamide-co-N-methyl-methacrylamide); poly(N-methyl-N-vinylacetamide-co-N-methoxymethyl-methacrylamide); poly(N-methyl-N-vinylacetamide-co-N-2-hydroxyethyl-methacrylamide); poly(N-methyl-N-vinylacetamide-co-1-vinyl-pyrrolidine-2,5-dione); poly(N-methyl-N-vinylacetamide-co-2-vinylene carbonate); or salts thereof.

In other embodiments, the polymer of the invention is a copolymer that is poly(N-vinylformamide-co-N-methyl-acrylamide); poly(N-vinylformamide-co-N,N-diethyl-acrylamide); poly(N-vinylformamide-co-N-methoxymethyl-acrylamide); poly(N-vinylformamide-co-N-methoxy-acrylamide); poly(N-vinylformamide-co-N-2-hydroxyethyl-acrylamide); poly(N-vinylformamide-co-N-methyl-methacrylamide); poly(N-vinylformamide-co-N,N-dimethyl-methacrylamide); poly(N-vinylformamide-co-N-methoxymethyl-methacrylamide); poly(N-vinylformamide-co-N-2-hydroxyethyl-methacrylamide); poly(N-vinylformamide-co-1-vinyl-pyrrolidine-2,5-dione); poly(N-vinylformamide-co-2-vinylene carbonate); poly(N- vinylformamide-co-vinyl acetate-co-2-vinylene carbonate); poly(N-methyl-N-vinylacetamide-co-N-methyl-acrylamide); poly(N-methyl-N-vinylacetamide-co-N,N-diethylacrylamide); poly(N-methyl-N-vinylacetamide-co-N-methoxymethyl-acrylamide); poly(N-methyl-N-vinylacetamide-co-N-methoxy-acrylamide); poly(N-methyl-N-vinylacetamide-co-N-2-hydroxyethyl-acrylamide); poly(N-methyl-N-vinylacetamide-co-N-methyl-methacrylamide); poly(N-methyl-N-vinylacetamide-co-N,N-dimethyl-methacrylamide); poly(N-methyl-N-vinylacetamide-co-N-methoxymethyl-methacrylamide); poly(N-methyl-N-vinylacetamide-co-N-2-hydroxyethyl-methacrylamide); poly(N-methyl-N-vinylacetamide-co-1-vinyl-pyrrolidine-2,5-dione); poly(N-methyl-N-vinylacetamide-co-2-vinylene carbonate); poly(N-methyl-N-vinylacetamide-co-vinyl acetate-co-2-vinylene carbonate); or salts thereof.

In other embodiments, the polymer of the invention is a copolymer that is poly(N-vinylformamide-co-N-methoxymethyl-acrylamide); poly(N-vinylformamide-co-N-methoxy-acrylamide); poly(N-vinylformamide-co-N-2-hydroxyethyl-acrylamide); poly(N-vinylformamide-co-N-methyl-methacrylamide); poly(N-vinylformamide-co-N-methoxymethyl-methacrylamide); poly(N-vinylformamide-co-N-2-hydroxyethyl-methacrylamide); poly(N-vinylformamide-co-1-vinyl-pyrrolidine-2,5-dione); poly(N-vinylformamide-co-2-vinylene carbonate); poly(N-methyl-N-vinylacetamide-co-N-methoxymethyl-acrylamide); poly(N-methyl-N-vinylacetamide-co-N-methoxy-acrylamide); poly(N-methyl-N-vinylacetamide-co-N-2-hydroxyethyl-acrylamide); poly(N-methyl-N-vinylacetamide-co-N-methyl-methacrylamide); poly(N-methyl-N-vinylacetamide-co-N-methoxymethyl-methacrylamide); poly(N-methyl-N-vinylacetamide-co-N-2-hydroxyethyl-methacrylamide); poly(N-methyl-N-vinylacetamide-co-1-vinyl-pyrrolidine-2,5-dione); poly(N-methyl-N-vinylacetamide-co-2-vinylene carbonate); or salts thereof.

As used herein, "—($C_1$-$C_{10}$ alkyl)" means a saturated straight chain or branched non-cyclic hydrocarbon having from 1 to 10 carbon atoms. Representative saturated straight chain —($C_1$-$C_{10}$ alkyls) include -methyl, -ethyl, —N-propyl, —N-butyl, —N-pentyl, —N-hexyl, —N-heptyl, —N-octyl, —N-nonyl, and —N-decyl. Representative saturated branched —($C_1$-$C_{10}$ alkyls) include -isopropyl, -sec-butyl, -iso-butyl, -tert-butyl, -isopentyl, -2-methylbutyl, -3-methylbutyl, -2,2-dimethylbutyl, -2,3-dimethylbutyl, -2-methylpentyl, -3-methylpentyl, -4-methylpentyl, -2-methylhexyl, -3-methylhexyl, -4-methylhexyl, -5-methylhexyl, -2,3-dimethylbutyl, -2,3-dimethylpentyl, -2,4-dimethylpentyl, -2,3-dimethylhexyl, -2,4-dimethylhexyl, -2,5-dimethylhexyl, -2,2-dimethylpentyl, -2,2-dimethylhexyl, -3,3-dimethylpentyl, -3,3-dimethylhexyl, -4,4-dimethylhexyl, -2-ethylpentyl, -3-ethylpentyl, -2-ethylhexyl, -3-ethylhexyl, -4-ethylhexyl, -2-methyl-2-ethylpentyl, -2-methyl-3-ethylpentyl, -2-methyl-4-ethylpentyl, -2-methyl-2-ethylhexyl, -2-methyl-3-ethylhexyl, -2-methyl-4-ethylhexyl, -2,2-diethylpentyl, -3,3-diethylhexyl, -2,2-diethylhexyl, -3,3-diethylhexyl and the like.

As used herein, "—($C_1$-$C_4$ alkyl)" means a saturated straight chain or branched non-cyclic hydrocarbon having from 1 to 4 carbon atoms. Representative saturated straight chain —($C_1$-$C_4$ alkyls) include -methyl, -ethyl, —N-propyl, and —N-butyl. Representative saturated branched —($C_1$-$C_4$ alkyls) include -isopropyl, -sec-butyl, -iso-butyl, and -tert-butyl.

As used herein, "—($C_1$-$C_{10}$ heteroalkyl)" broadly refers to a —($C_1$-$C_{10}$ alkyl) where up to three carbon atoms are replaced by and/or substituted with a heteroatom. Thus, a —($C_1$-$C_{10}$ heteroalkyl) possesses in-chain, pendant and/or terminal functionality, as understood by those persons skilled in the relevant art. As examples of in-chain functionality can be mentioned a carbonyl group or groups (which is/are, of course, included in the carbon count), heteroatom or heteroatoms (such as at least one oxygen, sulfur, nitrogen, phosphorous or silicon) in the chain, esters, amides, urethanes and their thio-derivatives, i.e., where at least one oxygen atom is replaced by a sulfur atom. As examples of pendant and/or terminal functionality can be mentioned groups such as hydroxyl, amino, cyano, aldehyde, carboxyl, esters of carboxyl, thio, thiocarboxyl, esters of thiocarboxyl, amido, and halogen. Thus, exemplary —($C_1$-$C_{10}$ heteroalkyl) groups include methoxy; ethoxy; propoxy; butoxymethyl; dimethoxybutyl; dimethoxyethyl; 3-(trimethylammonium chloride)-propyl; acetyl; cyanomethyl; cyanoethyl; 2-methoxyethyl; glycolic acid; glycolic acid esters, such as methyl ester; hydroxymethyl; methoxymethyl; methoxypropyl; 2,2,2-trichloro-1-hydroxyethyl; tri(hydroxymethyl)-methyl; pentafluoroethyl; 3-iodopropyl and the like.

As used herein, "—($C_3$-$C_8$ cycloalkyl)" means a saturated cyclic hydrocarbon having from 3 to 8 carbon atoms. Representative —($C_3$-$C_8$ cycloalkyls) include -cyclopropyl, -cyclobutyl, -cyclopentyl, -cyclohexyl, -cycloheptyl and -cyclooctyl.

As used herein, "-(3- to 8-membered heterocycloalkyl)" broadly refers to an aliphatic heterocycle ring of 3 to 8 members where at least one carbon atom is replaced with a heteroatom that is independently nitrogen, oxygen or sulfur. A -(3-membered heterocycloalkyl)'s ring can have one heteroatom. A -(4- to 5-membered heterocycloalkyl)'s ring can have one or two heteroatoms. A -(6- to 8-membered heterocycloalkyl)'s ring can have one, two or three heteroatoms. Representative -(3- to 8-membered heterocycloalkyl)s include epoxide, 1,4-dioxane, tetrahydrofuran, morpholine, 1H-azepine, piperidine, piperazine, tetrahydrothiophene, thiomorpholine and the like.

As used herein, "aryl" refers phenyl, naphthyl, anthryl and phenanthryl.

As used herein, "-(5- to 10-membered heteroaryl)" means an aromatic heterocycle ring of 5 to 10 members, including both mono- and bicyclic ring systems, where at least one carbon atom of one or both of the rings is replaced with a heteroatom that is independently nitrogen, oxygen, or sulfur. One or both of the -(5- to 10-membered heteroaryl)'s rings contain at least one carbon atom. Representative (5- to 10-membered heteroaryl)s include pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl and quinazolinyl.

As used herein, a "compound term," e.g., —($C_3$-$C_8$ cycloalkyl)($C_1$-$C_{10}$ heteroalkyl), broadly refers to a monovalent first group, here $C_3$-$C_8$ cycloalkyl, in which the valency is derived by abstraction of a hydrogen from a carbon atom or heteroatom, where the first group is further substituted with one or more second group(s), here a $C_1$-$C_{10}$ heteroalkyl group(s), e.g., 3-chloromethylcyclohexyl or 3,4-di(chloromethyl)cyclohexyl. As a further illustration, a compound term such as —($C_1$-$C_{10}$ alkyl)(aryl) refers to a first group, here $C_1$-$C_{10}$ alkyl, which is further substituted with one or more second group(s), here an aryl group(s). Illustrative —($C_1$-$C_{10}$ alkyl)(aryl) groups are benzyl and 2,2-diphenyl ethyl.

As used herein, a "salt" of a polymer refers to a polymer having at least one anionic charge, cationic charge, or both, e.g., an amphoteric polymer, where each charge has associated with it a counterion. "Counterion" refers to an ion that balances the polymer's anionic or cationic charge. Exemplary counterions for a polymer comprising a cationic charge include chloride, bromide, iodide, hydroxide, alkoxide, carbonate, bicarbonate, oxide, formate, sulfate, benzene sulfonate, p-toluenesulfonate, p-bromobenzenesulfonate, methanesulfonate, trifluoromethanesulfonate, phosphate, perchlorate, tetrafluoroborate, tetraphenylboride, nitrate and anions of aromatic or aliphatic carboxylic acids. Exemplary counterions for a polymer comprising an anionic charge include $NH_4^+$, tetraalkyl ammonium, quaternary phosphonium, such as a tetraalkyl phosphonium halide, triethyl amine, trimethyl amine and 2-amino-2-(hydroxymethyl)-1,3-propanediol ("TRIS"), and the cations of Li, Na, K, Rb, Cs and Ag. In certain embodiments, the counterions include chloride, p-toluenesulfonate, lithium, sodium and potassium.

In one embodiment, a polymer of the invention is a random copolymer. In another embodiment, a polymer of the invention is a substantially random copolymer, i.e., the polymer of the invention has more random copolymer units that alternating copolymer units. In another embodiment, a polymer of the invention is a nearly random copolymer, i.e., when the copolymerization by which the polymer of the invention is formed is stopped at a conversion of less than 50 mol % of the total monomer content, the polymer of the invention has more random copolymer units that alternating copolymer units.

In one embodiment, a polymer of the invention is water soluble, water-swellable, or both, at atmospheric pressure, a concentration of from about 0.01 to about 1 wt. %, and from about 20° C. to about 70° C. in water. In another embodiment, a polymer of the invention is water soluble, water-swellable, or both, at about 25° C. in water. For purposes of this invention, water-swellable polymers of the invention are generally those that swell in water but are not completely soluble because they have a very slow dissolution rate, e.g., polymers that are substantially uncrosslinked but have an extremely high weight-average molecular weight ("Mw"); or those unable to dissolve completely in water because they have been crosslinked to a certain low degree, for example, when a polymer of the invention comprises an amount of a crosslinking or branching agent. In one embodiment, a polymer of the invention is able to flow into or out of a capillary either with or without the assistance of pressure or vacuum. In another embodiment, a polymer of the invention is uncrosslinked. In another embodiment, a polymer of the invention is substantially uncrosslinked.

The Mw of a polymer of the invention can vary widely. In one embodiment, the Mw of a polymer of the invention is at least about 150,000 Daltons. In another embodiment, the Mw of a polymer of the invention is at least about 200,000 Da. In another embodiment, the Mw of a polymer of the invention is at least about 500,000 Da. In another embodiment, the Mw of a polymer of the invention is at least about 1 MDaltons. In another embodiment, the Mw of a polymer of the invention is at least about 2 MDa. In another embodiment, the Mw of a polymer of the invention is from about 150,000 Da to about 20 MDa. In another embodiment, the Mw of a polymer of the invention is from about 500,000 Da to about 10 MDa. In another embodiment, the Mw of a polymer of the invention is from about 1 MDa to about 20 MDa. In another embodiment, the Mw of a polymer of the invention is from about 1 MDa to about 5 MDa. In another embodiment, the Mw of a polymer of the invention is from about 500,000 Da to about 5 MDa.

The molecular weight of a polymer of the invention can be determined using conventional methods. The conventional method of gel permeation chromatography ("GPC"), also known as size exclusion chromatography or SEC, is a way for determining the molecular weight of polymers and copolymers. The fundamentals of applying a multi-angle laser light scattering detector to GPC instrumentation ("GPC-MALLS") for the absolute characterization of polymers, such as the determination of their number-average and weight-average molecular weights, are conventional, e.g, see Wyatt, *Analytica Chimica Acta* 272:1-40 (1993). For example, GPC-MALLS has been used to determine, inter alia, the Mw of several water-soluble polymers and copolymers having molecular weights of from below 50,000 Da to over 1 MDa. Nagy, *Proc. Int'l. GPC Symposium*, Orlando, Fla., June 1994 95-0315:71-95 (1994). Moreover, the use of GPC and, in particular, GPC-MALLS, for molecular weight determinations is well-recognized in the art. For example, the GPC molecular weight results obtained for identical polymer samples using several different advanced on-line detection systems, including GPC-MALLS compare favorably. S. Yau, *Chemtracts—Macromolecular Chemistry* 1:1-36 (1990). Therefore, GPC-MALLS is a conventional way for determining the number-average ("Mn") and weight-average molecular weights of a polymer of the invention.

4.2. Method for Making Polymers of the Invention

Many methods of making polymers are known in the art and can be used to prepare the polymer of the invention. Such polymerizations can be conducted in bulk, solution, suspension, emulsion or microemulsion, and a wide variety of polymerization initiators can be used. For example, several such methods are summarized in the following chapter: C. A. Costello et al., *Copolymers in Kirk-Othmer Encyc. of Chem. Technol.* Vol. 7, 349-381 (4$^{th}$ ed. 1993).

Thus, a second embodiment of the invention relates to a method for making a polymer of the invention, comprising the step of polymerizing an $M_1$, optionally in the presence of an $M_2$, to provide a polymer of the invention. It is to be understood that a polymer of the invention can be a homopolymer or a copolymer. The polymerization can be initiated by at least one free-radical, anionic and/or cationic initiator. In another embodiment, the polymerization is initiated by at least one free-radical initiator. The free-radical initiator can be dissociated thermally or photolytically in initiating the polymerization. In another embodiment, the present invention relates to the polymer of the invention product of any of the methods herein for making it.

A polymerization reaction can be carried out by conventional methods, e.g., by free-radical initiation of monomer(s), thereby forming the polymer of the invention. Without being bound by a particular theory, a proposed mechanism for polymerization yielding an exemplary polymer of the invention is shown in the following Scheme 1. Free-radicals formed, for example, by the thermal or photolytic decomposition of a free-radical initiator at the start of polymerization, can initiate the polymerization of monomer (I) to form polymer (P).

Scheme 1

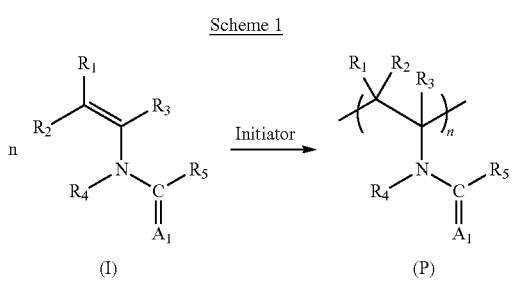

In another embodiment of a method for making a polymer of the invention, $M_1$ is N-vinylformamide ("VF") (III), N-vinylacetamide (IV), N-methyl-N-vinylacetamide ("MVA") (V), or a mixture thereof, each of these monomers being illustrated in the following Scheme 2.

Scheme 2

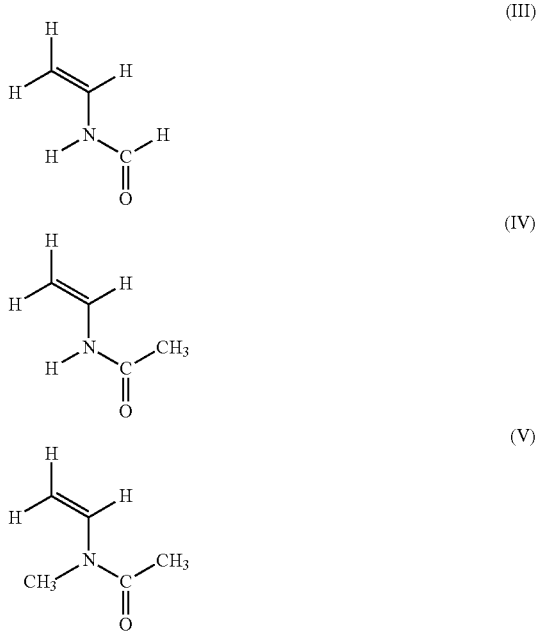

In another embodiment, the comonomers for making a polymer of the invention can be water-soluble.

In another embodiment, the free-radical initiator(s) for making the polymer of the invention are thermally or photolytically dissociated initiators selected from azo compounds, diazo compounds, organic peroxides, organic hydroperoxides, organic persulfates, organic hydropersulfates, inorganic peroxides, inorganic persulfates, peroxide-redox systems, carbon-carbon initiators, photoinitiators, or a mixture thereof.

Many types of free-radical initiators can be used, e.g., azo and diazo compounds, such as azo-bis-isobutyronitrile ("AIBN"), organic peroxides, hydroperoxides, persulfates and hydropersulfates, such as benzoyl peroxide, inorganic peroxides and persulfates, such as the peroxide-redox systems, carbon-carbon initiators, such as hexasubstituted ethanes, and photoinitiators; numerous examples are known in the art. See Sanchez et al., *Initiators (Free-Radical) in Kirk-Othmer Encyc. of Chem. Technol*. Vol. 14, 431-460 (4th ed. 1993). Anionic initiators are known in the art and include aromatic radical anions, such as sodium naphthalene; alkyl lithium compounds, such as t-butyl lithium; fluorenyl carbanions; 1,1-diphenylmethylcarbanions; cumyl potassium; and those described by Quirk et al., *Initiators (Anionic) in Kirk-Othmer Encyc. of Chem. Technol*. Vol. 14, 461-476 (4th ed. 1993). Cationic initiators are also known in the art and include protic acids, cation donor (initiator)/Friedel-Crafts acid (coinitiator) systems, stable cation salts, and those described by Faust, *Initiators (Cationic) in Kirk-Othmer Encyc. of Chem. Technol*. Vol. 14, 476-482 (4th ed. 1995). The free-radical, anionic or cationic initiator can undergo decomposition by any known means, e.g., thermally or photolytically, when this is required to initiate polymerization.

In another embodiment, the polymer of the invention can be prepared using free-radical polymerization in aqueous solution.

In another embodiment, the polymer of the invention can be prepared using aqueous solution free-radical polymerization with at least one a water-soluble azo initiator.

Of course, other ways for initiating polymerization known in the art can also be used to make the polymer of the invention. For example, exposing a combination of $M_1$ and, optionally, any other monomer(s) to an electron beam, ultraviolet radiation, usually in the presence of a photoinitiator, and high energy ionizing radiation sources, such as γ-radiation from a $^{60}Co$ or $^{137}Cs$ source, α-particles, β-particles, fast neutrons and x-rays, can cause the generation of free-radicals and/or ions that, in turN, initiate polymerization. Sanchez et al., *Initiators (Free-Radical)*" at 454-457; Sheppard et al., *Initiators in Kirk-Othmer Encyc. of Chem. Technol*. Vol. 13, 367-370 (3rd ed. 1981).

The Mw of the polymer of the invention can vary widely. Those skilled in the art will recognize that polymer of the invention having a particular Mw can be obtained using conventional methods, e.g., using a chain transfer agent, such as N-butanol or isopropanol, and/or varying the amount of chain transfer agent present. The Mw can be increased by decreasing the initiator concentration relative to the starting monomer concentration and/or decreasing the amount of chain transfer agent present, or even eliminating the chain transfer agent entirely.

The polymer of the invention can be prepared using the method of inverse emulsion polymerization ("IEP"). Many aspects of the IEP method have been described in detail by, e.g., "Inverse Emulsion (Microemulsion) Polymerization," Chapter 4 in *Radical Polymerization in Disperse Systems*, Barton et al., Ellis Horwood, New York, 1994, pp. 187-215; Candau et al., *J. Polym. Sci., Polym. Chem. Ed.*, 23:193-214 (1985); and Pross et al., *Polym. Int'l.*, 45:22-26 (1998). IEP is sometimes referred to as inverse microsuspension polymerization (Pross, p. 22.) or as inverse microemulsion polymerization (Barton, Id.).

Any oil can be used to form the inverse emulsion. To make polymer of the invention from an N-vinylamide-type monomer(s), the N-vinylamide should be present in the water phase. Without being bound by a particular theory, because N-vinylamides are partially soluble in the oils commonly used in the art as the oil phase for IEP, its oil-solubility is thought to limit the maximum molecular weight of the polymer produced when using such oils. Thus, when polymers of the invention are to be made, it is desirable, but not required, that their monomer(s) be substantially insoluble in the oil selected.

For the purpose of selecting an appropriate monomer/oil combination, "oil insoluble" is defined as follows. At a temperature of 20° C. throughout, 1 mL of the selected monomer or monomer mixture is placed into 6 mL of the selected oil(s) and vortex mixed for 1 minute. The mixing is stopped and the liquid is allowed to stand for 10 minutes. The monomer(s) is oil insoluble if phase separation, e.g., translucency, cloudiness and/or separate layers, can be observed with the unaided eye after the 10 minute period. Conversely, the monomer(s) is not oil insoluble if no phase separation, i.e., a clear solution, is observed after the 10 minute period.

For example, by this test N-vinylamides were determined to be not oil insoluble in each of acetonitrile, acetone, methanol, 1-decanol, ethyl ether, hexane, decane, petroleum ether (normal boiling range 35-60° C.), and petroleum special (normal boiling range 180-220° C.). However, N-vinylamides were determined to be oil insoluble by this test in, e.g., aliphatic hydrocarbons comprising at least about 15 carbon atoms. In addition, N-vinylamides were determined to be oil insoluble by this test in, e.g., aliphatic hydrocarbons with a normal boiling point at or above about 270° C. Exemplary hydrocarbons that are can be used as oils for forming the N-vinylamide polymers and copolymers of the invention by IEP from N-vinylamides include pentadecane, hexadecane, heptadecane, white light mineral or paraffin oils, white heavy mineral or paraffin oils, and mineral or paraffin oils for Nujol preparations.

N-vinylamides are also oil insoluble using the above test in, e.g., silicone oils, at least partially fluorinated hydrocarbons and liquid perfluoropolyethers ("PFPE"), also known as perfluoropolyalkylethers ("PFPAE").

Exemplary silicones that are conventional and can be used as oils for forming the polymer of the invention by IEP from include poly(dimethylsiloxane)-based oils such as DC200, DC510, DC550 and DC710, each of which can be available in various viscosity grades (e.g., from 10 cSt to 12,500 cSt for DC200) from Dow Corning and poly(methylphenylsiloxane)-based oils such as AR200, also from Dow Corning.

Exemplary at least partially fluorinated hydrocarbon liquids that are conventional and can be used as oils for forming the polymer of the invention by IEP include the FLUORINERT series available from 3M, e.g., FC-40, FC-43, FC-70, FC-72, FC-77, FC-84, FC-87, FC-3283, FC-5312 and FC-5320

Exemplary liquid PFPEs that are conventional and can be used as oils for forming the polymer of the invention by IEP include the DEMNUIM series available from Daikin Industries, Ltd., e.g., S-20, S-65, S-100 and S-200, the KRYTOX series available from DuPont, e.g., GPL100, GPL101, GPL102, GPL103, GPL104, GPL105, GPL106, GPL107, 143AB, 143AC and VPF1525, and the FOMBLIN Y, Z and M series available from Ausimont Montedison Group, e.g., Y04, Y06, Y25, Y-L VAC 25/6, YR, YR1500, YR1800, Z03, Z15, Z25, Z60, M03, M15, M30 and M60. As disclosed by, e.g., Hamada, *Phys. Chem. Chem. Phys.*, 2:115-122 (2000), the DEMNUIM-type PFPEs have the formula F—[CF$_2$CF$_2$CF$_2$O]$_n$—H, the KRYTOX-type PFPEs have the formula F—[CF(CF$_3$)CF$_2$O]$_l$—H, and the FOMBLIN-Z-type PFPEs have the formula F—[(CF$_2$CF$_2$O)$_2$—(CF$_2$O)]$_m$—H, where n, l and m are varied to give, e.g., different chain lengths and viscosities.

In one embodiment, oils for the IEP of N-vinylamides to obtain polymer of the invention include aliphatic hydrocarbons comprising at least about 15 carbon atoms, aliphatic hydrocarbons having a normal boiling point at or above about 270° C., silicone oils, at least partially fluorinated hydrocarbons, liquid perfluoropolyethers, or a mixture thereof. In another embodiment, oils for the IEP of N-vinylamides to obtain polymer of the invention include pentadecane, hexadecane, heptadecane, white light mineral oils, white heavy mineral oils, and mineral oils for Nujol preparations. In another embodiment, the oil used for the IEP of N-vinylamides to obtain the polymer of the invention is a mineral oil for Nujol preparations.

At least one surfactant can be used to form the inverse emulsion. When an additional surfactant is present, the additional surfactant is sometimes known as a cosurfactant. It is conventional to characterize a surfactant by its hydrophilic lipophilic balance ("HLB"), a measure of the relative simultaneous attraction of the surfactant for water or oil. On the HLB scale ranging from 1 to 40, relatively lipophilic surfactants have a low numerical value while relatively hydrophilic surfactants have a high numerical value.

A wide variety of surfactants are known to be available, for example, many are listed with HLB values in *McCutcheon's Emulsifiers & Detergents*, North American Ed., Manufacturing Confectioner Pub. Co., Glen Rock, N.J., 1988, pp. 1-217. The surfactant can be nonionic or have an anionic charge, cationic charge, or both, e.g., an amphoteric surfactant, where each charge has associated with it a counterion; numerous examples of each are known in the art. See Lyn N, Jr. et al., *Surfactants in Kirk-Othmer Encyc. of Chem. Technol*. Vol. 23, 483-541 (4$^{th}$ ed. 1997).

Nonionic surfactants are known in the art and include polyoxyethylene surfactants, e.g., alcohol ethoxylates and alkylphenol ethoxylates; carboxylic acid esters, e.g., glycerol esters and polyoxyethylene esters; anhydrosorbitol esters, e.g., mono-, di- and tri-esters of sorbitan and fatty acids; polyalkylene oxide block copolymers; and poly(oxyethylene-co-oxypropylene) nonionic surfactants. Id., pp. 506-523.

Anionic surfactants are known in the art and include carboxylates, e.g., soaps, polyalkoxycarboxylates and N-acylsarcosinates; sulfonates, e.g., alkylbenzene sulfonates, naphthalene sulfonates and petroleum sulfonates; sulfates, e.g., alcohol sulfates and ethoxylated and sulfated alcohols; and phosphates, e.g., phosphate esters. Id., pp. 491-505.

Cationic surfactants are known in the art and include amines, e.g., aliphatic mono-, di- and polyamines derived from fatty and rosin acids; and quaternary ammonium salts, e.g., dialkyldimethyl and alkyltrimethyl ammonium salts, alkylbenzyldimethyl ammonium chlorides, and alkylpyridinium halides. Id., pp. 524-530. Amphoteric surfactants are known in the art and include alkylbetaines, amidopropylbetaines and imidazolinium derivatives. Id., pp. 530-532.

Considerations typically taken into account in selecting a surfactant or surfactant blend to form an inverse emulsion are conventional and are summarized in, e.g., Griffin, *Emulsions in Kirk-Othmer Encyc. of Chem. Technol*. Vol. 8, 909-919 (3$^{rd}$ ed. 1979). Furthermore, it is recognized that some monomers, e.g., acrylamide, can sometimes act as a co-surfactant. Candau, p. 204; Barton, p. 191. In such cases, the overall HLB value of the emulsification system can differ from the HLB of the selected surfactant or surfactant blend. Barton, p. 191. Moreover, those in the art recognize that particular characteristics of the inverse emulsion must be taken into account when selecting a surfactant. For example, when a fluorinated oil is used, it is desirable to also select an at least partially fluorinated surfactant. Taking such conventional factors into consideration, one skilled in the art is able to select a wide variety of surfactants, used individually or in combination, for the IEP of water-soluble monomers to form high molecular weight polymers and, particularly, to form polymer of the invention from N-vinylamides by IEP.

In one embodiment, surfactants for the IEP of N-vinylamides to the polymer of the invention have an HLB of about 7 or less. In another embodiment, the surfactant HLB is about 6 or less. In another embodiment, the surfactant HLB is from about 3 to about 6. In another embodiment, surfactants for the IEP of N-vinylamides to the polymer of the invention have an HLB of from about 4 to about 6. In another embodiment, surfactants include SPAN-80 from Fluka, sorbitan monooleate thought to have the following structure:

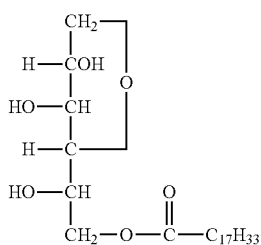

with a molecular weight of about 429 Da and an HLB of about 4.3; TETRONIC 1301 from BASF, an amine-based block copolymer nonionic surfactant thought to have the following structure:

with a molecular weight of about 6,800 Da and an HLB of about 2.0; or a mixture thereof.

A sufficient amount of the surfactant is used such that a stable emulsion or microemulsion is formed; routine experimentation by one skilled in the art can be used to determine that amount. To obtain, after polymerization, a microemulsion of high polymer content, the ratio (by weight) of aqueous phase to oil phase is usually chosen to be as high as possible. This ratio can range, for example, from about 1:10 to about 4:1. In another embodiment, the ratio can range from about 1:2 to about 3:1. In another embodiment, the quantity of solid polymer product is greater than about 10 wt. % of the total emulsion weight.

Many types of initiators discussed above can are be used for inverse emulsion polymerizations, e.g., free-radical initiators such as the azo compounds, organic peroxides and persulfates, inorganic peroxides and persulfates, and carbon-carbon initiators, as well as photoinitiators such as those described in McGinniss, *Radiation Curing in Kirk-Othmer Encyc. of Chem. Technol.* Vol. 20, 848-850 (4$^{th}$ ed. 1996). Polymerization can, of course, also be effected by high energy ionizing radiation sources.

In one embodiment, inverse emulsion polymerization initiators include the azo compounds, either the oil-soluble types such as AIBN or the water-soluble types such as azobutyroamidine, oil-soluble peroxides and persulfates, such as dibenzoyl peroxide, water soluble peroxides and persulfates, such as ammonium persulfate and potassium persulfate, redox initiating systems, which include the peroxy-redox types and, e.g., $K_2S_2O_8/Na_2S_2O_5$ or ferrous ammonium sulfate/ammonium persulfate, and photoinitiators, such as Michler's ketone, i.e., 4,4'-bis-(dimethylamino) benzophenone, and IRGACURE-1700 and DAROCURE-1173 from Ciba-Geigy, believed to be (25% bis-(2,6-dimethoxybenzoyl)-2,4,4-trimethylpentylphosphine oxide+ 75% 2-hydroxy-2-methyl-1-phenyl-propan-1-one) and 2-hydroxy-2-methyl-1-phenyl-propan-1-one, respectively. In another embodiment, initiators for the IEP of N-vinylamides to the N-vinylamide polymers and copolymers of the invention include oil-soluble azo compounds, water soluble peroxides and persulfates, redox initiating systems, photoinitiators, or a mixture thereof. In another embodiment, the initiator used for the IEP of N-vinylamides to the polymer of the invention is AIBN, ammonium persulfate, potassium persulfate, Michler's ketone, 2-hydroxy-2-methyl-1-phenyl-propan-1-one, bis-(2,6-dimethoxybenzoyl)-2,4,4-trimethylpentylphosphine oxide, or a mixture thereof.

The inverse emulsion and/or its aqueous phase can also contain such other additives if desired. These include chain transfer agents, pH adjusters, co-initiators, sensitizers, charge-transfer complexes or donor-acceptor complexes when photoinitiation is used, chelating agents for removing polymerization inhibitors, and other conventional additives used in their usual proportions. Polymerization in the inverse emulsion or microemulsion can be carried out by any manner known to those skilled in the art, e.g., as generally described in Griffin, pp. 919-923; U.S. Pat. No. 5,530,069 to Neff et al., at col. 3, lines 39-65 and col. 5, line 29 to col. 6, line 44; and in the references cited therein.

In another embodiment, the present invention relates to the polymer of the invention, methods for making the same, and polymer of the invention made by the methods disclosed herein.

4.3. Compositions of the Invention

A third embodiment of the invention relates to a composition comprising a polymer of the invention (e.g., see Section 4.1) and a buffer. The composition is useful as an electrophoresis separation medium. In some embodiments, the composition further comprises a second polymer or a salt thereof (described in further detail below). In another embodiment, the composition further comprises a denaturant. In the compositions, the polymer of the invention comprises one or more monomers of type $M_1$ and optionally one or more monomers of type $M_2$, such that:

(a) each monomer in the polymer is of type $M_1$ or $M_2$;

(b) x is an integer ranging from 1 to 5 and represents the number of monomer subtypes of type $M_1$ that are present in the polymer;

(c) y is an integer ranging from 0 to 5 and represents the number of monomer subtypes of type $M_2$ that are present in the polymer;

(d) each monomer subtype of type $M_1$ in the polymer independently has the formula (I):

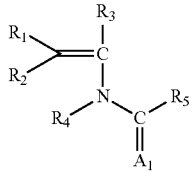

(I)

where each $A_1$ is independently =O, =S or =NX$_1$;
each of $R_1$, $R_2$, $R_3$ and $R_4$ is independently —H, —($C_1$-$C_{10}$ alkyl), —($C_3$-$C_8$ cycloalkyl), -(aryl), -(5- to 10-membered heteroaryl), —($C_1$-$C_{10}$ alkyl)(aryl) or -(aryl)($C_1$-$C_{10}$ alkyl);

each $R_5$ is independently —(H), —($C_1$-$C_{10}$ alkyl), —($C_1$-$C_{10}$ heteroalkyl), —($C_3$-$C_8$ cycloalkyl), -(3- to 8-membered heterocycloalkyl), -(aryl), -(5- to 10-membered heteroaryl), —($C_1$-$C_{10}$ alkyl)($C_3$-$C_8$ cycloalkyl), —($C_3$-$C_8$ cycloalkyl)($C_1$-$C_{10}$ alkyl), —($C_1$-$C_{10}$ heteroalkyl)($C_3$-$C_8$ cycloalkyl), —($C_3$-$C_8$ cycloalkyl)($C_1$-$C_{10}$ heteroalkyl), —($C_1$-$C_{10}$ alkyl)(3- to 8-membered heterocycloalkyl), -(3- to 8-membered heterocycloalkyl)($C_1$-$C_{10}$ alkyl), —($C_1$-$C_{10}$ heteroalkyl)(3- to 8-membered heterocycloalkyl), -(3- to 8-membered heterocycloalkyl)($C_1$-$C_{10}$ heteroalkyl), —($C_1$-$C_{10}$ alkyl)(aryl), -(aryl)($C_1$-$C_{10}$ alkyl), —($C_1$-$C_{10}$ heteroalkyl)(aryl), -(aryl)($C_1$-$C_{10}$ heteroalkyl), —($C_1$-$C_{10}$ alkyl)(5- to 10-membered heteroaryl), -(5- to 10-membered heteroaryl)($C_1$-$C_{10}$ alkyl), —($C_1$-$C_{10}$ heteroalkyl)(5- to 10-membered heteroaryl), -(5- to 10-membered heteroaryl)($C_1$-$C_{10}$ heteroalkyl), —($C_1$-$C_4$ alkyl)$_p$NH$_2$, —($C_1$-$C_4$ alkyl)$_p$CONH$_2$, —($C_1$-$C_4$ alkyl)NHCONH$_2$, —($C_1$-$C_4$ alkyl)NHCOH or —($C_1$-$C_4$ alkyl)$_p$NHCOCH$_3$, where each p is 0 or 1; and each $X_1$ is independently —H, —($C_1$-$C_{10}$ alkyl), —($C_3$-$C_8$ cycloalkyl), -(aryl), -(5- to 10-membered heteroaryl), —($C_1$-$C_{10}$ alkyl)(aryl), -(aryl)($C_1$-$C_{10}$ alkyl), —($C_1$-$C_4$ alkyl)$_p$NH$_2$, —($C_1$-$C_4$ alkyl)$_p$CONH$_2$, —($C_1$-$C_4$ alkyl)NHCONH$_2$, —($C_1$-$C_4$ alkyl)$_p$NHCOH or —($C_1$-$C_4$ alkyl)$_p$NHCOCH$_3$, where each p is 0 or 1; and (e) when y is not zero, each monomer subtype of type $M_2$ in the polymer is independently:
1-vinyl-pyrrolidine-2,5-dione;
3-vinyl-oxazolidin-2-one;
1-vinyl-imidazolidin-2-one;
4-vinyl-morpholin-3,5-dione;
4-vinyl-morpholin-3-one;
4-vinyl-morpholine;
2-vinyl-1,3-dioxolane;
2-vinylene carbonate;
methoxyethylene;
vinyl acetate;
vinyl alcohol;

a monomer of formula (II):

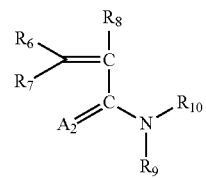

(II)

where each $A_2$ is independently =O, =S or =NX$_2$;
each of $R_6$, $R_7$, $R_8$ and $R_9$ is independently —H, —($C_1$-$C_{10}$ alkyl), —($C_3$-$C_8$ cycloalkyl), -(aryl), -(5- to 10-membered heteroaryl), —($C_1$-$C_{10}$ alkyl)(aryl) or -(aryl)($C_1$-$C_{10}$ alkyl);
each $R_{10}$ is independently —H, —OH, —($C_1$-$C_{10}$ alkyl), —($C_1$-$C_{10}$ heteroalkyl), —($C_3$-$C_8$ cycloalkyl), -(3- to 8-membered heterocycloalkyl), -(aryl), -(5- to 10-membered heteroaryl), —($C_1$-$C_{10}$ alkyl)($C_3$-$C_8$ cycloalkyl), —($C_3$-$C_8$ cycloalkyl)($C_1$-$C_{10}$ alkyl), —($C_1$-$C_{10}$ heteroalkyl)($C_3$-$C_8$ cycloalkyl), —($C_4$-$C_8$ cycloalkyl)($C_1$-$C_{10}$ heteroalkyl), —($C_1$-$C_{10}$ alkyl)(3- to 8-membered heterocycloalkyl), -(3- to 8-membered heterocycloalkyl)($C_1$-$C_{10}$ alkyl), —($C_1$-$C_{10}$ heteroalkyl)(3- to 8-membered heterocycloalkyl), -(3- to 8-membered heterocycloalkyl)($C_1$-$C_{10}$ heteroalkyl), —($C_1$-$C_{10}$ alkyl)(aryl), -(aryl)($C_1$-$C_{10}$ alkyl), —($C_1$-$C_{10}$ heteroalkyl)(aryl), -(aryl)($C_1$-$C_{10}$ heteroalkyl), —($C_1$-$C_{10}$ alkyl)(5- to 10-membered heteroaryl), -(5- to 10-membered heteroaryl)($C_1$-$C_{10}$ alkyl), —($C_1$-$C_{10}$ heteroalkyl)(5- to 10-membered heteroaryl), -(5- to 10-membered heteroaryl)($C_1$-$C_{10}$ heteroalkyl), —($C_1$-$C_4$ alkyl)$_q$NH$_2$, —($C_1$-$C_4$ alkyl)$_q$CONH$_2$, —($C_1$-$C_4$ alkyl)NHCONH$_2$, —($C_1$-$C_4$ alkyl)NHCOH, —($C_1$-$C_4$ alkyl)$_q$NHCOCH$_3$ or a group of formula (III):

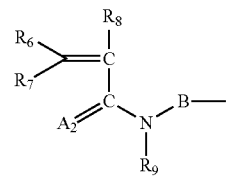

(III)

where B is —CH$_2$—, —CH$_2$—CH$_2$—, —CH$_2$—CH$_2$—CH$_2$—, —CH(CH$_3$)—CH$_2$— or —CH$_2$—CH(CH$_3$)—, and each q is 0 or 1; and each $X_2$ is independently —H, —OH, —($C_1$-$C_{10}$ alkyl), —($C_1$-$C_{10}$ heteroalkyl), —($C_3$-$C_8$ cycloalkyl), -(aryl), -(5- to 10-membered heteroaryl), —($C_1$-$C_{10}$ alkyl)(aryl), -(aryl)($C_1$-$C_{10}$ alkyl), —($C_1$-$C_4$ alkyl)$_q$NH$_2$, —($C_1$-$C_4$ alkyl)$_q$CONH$_2$, —($C_1$-$C_4$ alkyl)NHCONH$_2$, —($C_1$-$C_4$ alkyl)$_q$NHCOH or —($C_1$-$C_4$ alkyl)$_q$NHCOCH$_3$, where each q is 0 or 1; or mixtures thereof;

(f) provided that when x is 1 and y is 0, $M_1$ is not N-vinylacetamide, N-vinylpropamide, N-vinylbutamide or N-vinylpentamide.

In certain embodiments, x is 1 and y is 0.
In certain embodiments, x is 2 and y is 0.
In certain embodiments, x is 3 and y is 0.
In certain embodiments, x is 4 and y is 0.
In certain embodiments, x is 5 and y is 0.

In certain embodiments, x is 1 and y is 1.
In certain embodiments, x is 2 and y is 1.
In certain embodiments, x is 3 and y is 1.
In certain embodiments, x is 4 and y is 1.
In certain embodiments, x is 5 and y is 1.
In certain embodiments, x is 1 and y is 2.
In certain embodiments, x is 2 and y is 2.
In certain embodiments, x is 3 and y is 2.
In certain embodiments, x is 4 and y is 2.
In certain embodiments, x is 5 and y is 2.
In certain embodiments, x is 1 and y is 3.
In certain embodiments, x is 2 and y is 3.
In certain embodiments, x is 3 and y is 3.
In certain embodiments, x is 4 and y is 3.
In certain embodiments, x is 5 and y is 3.
In certain embodiments, x is 1 and y is 4.
In certain embodiments, x is 2 and y is 4.
In certain embodiments, x is 3 and y is 4.
In certain embodiments, x is 4 and y is 4.
In certain embodiments, x is 5 and y is 4.
In certain embodiments, x is 1 and y is 5.
In certain embodiments, x is 2 and y is 5.
In certain embodiments, x is 3 and y is 5.
In certain embodiments, x is 4 and y is 5.
In certain embodiments, x is 5 and y is 5.
In certain embodiments, y is 0 and, for each monomer subtype of type $M_1$:
$A_1$ is O;
$R_1$ and $R_2$ are H; and
each $R_3$ is independently H or methyl.
In other embodiments y is 0 and, for each monomer subtype of type $M_1$:
$A_1$ is O;
$R_1$ and $R_2$ are H;
each $R_3$, $R_4$ and $R_5$ is independently H or methyl.
In another embodiment, y is 0 and, for each monomer subtype of type $M_1$:
$A_1$ is 0; and
$R_1$, $R_2$, $R_3$, $R_4$ and $R_5$ are H.
In another embodiment, y is 0 and, for each monomer subtype of type $M_1$:
$A_1$ is O;
$R_1$, $R_2$, $R_3$, and $R_4$ are H; and
$R_5$ is methyl.
In another embodiment, y is 0 and, for each monomer subtype of type $M_1$:
$A_1$ is O;
$R_1$, $R_2$ and $R_3$ are H; and
$R_4$ and $R_5$ are methyl.
In certain embodiments, y is 0, x is 2 and, for each monomer subtype of type $M_1$:
$A_1$ is O;
$R_1$ and $R_2$ are H; and
each $R_3$ is independently H or methyl.
In other embodiments, y is 0, x is 2 and, for each monomer subtype of type $M_1$:
$A_1$ is O;
$R_1$ and $R_2$ are H;
each $R_3$, $R_4$ and $R_5$ is independently H or methyl.
In another embodiment, y is 0, x is 2 and, for each monomer subtype of type $M_1$:
$A_1$ is 0; and
$R_1$, $R_2$, $R_3$, $R_4$ and $R_5$ are H.
In another embodiment, y is 0, x is 2 and, for each monomer subtype of type $M_1$:
$A_1$ is O;
$R_1$, $R_2$, $R_3$, and $R_4$ are H; and
$R_5$ is methyl.
In another embodiment, y is 0, x is 2 and, for each monomer subtype of type $M_1$:
$A_1$ is O;
$R_1$, $R_2$ and $R_3$ are H; and
$R_4$ and $R_5$ are methyl.
In certain embodiments, y is 0, x is 1 and, for $M_1$:
$A_1$ is O;
$R_1$ and $R_2$ are H; and
each $R_3$ is independently H or methyl.
In other embodiments, y is 0, x is 1 and, for $M_1$:
$A_1$ is O;
$R_1$ and $R_2$ are H;
each $R_3$, $R_4$ and $R_5$ is independently H or methyl.
In another embodiment, y is 0, x is 1 and, for $M_1$:
$A_1$ is 0; and
$R_1$, $R_2$, $R_3$, $R_4$ and $R_5$ are H.
In another embodiment, y is 0, x is 1 and, for $M_1$:
$A_1$ is O;
$R_1$, $R_2$, $R_3$, and $R_4$ are H; and
$R_5$ is methyl.
In another embodiment, y is 0, x is 1 and, for $M_1$:
$A_1$ is O;
$R_1$, $R_2$ and $R_3$ are H; and
$R_4$ and $R_5$ are methyl.
In certain embodiments:
(a) for each monomer subtype of type $M_1$:
$A_1$ is O;
$R_1$ and $R_2$ are H; and
each $R_3$ is independently H or methyl;
(b) y is 2; and
(c) for each monomer subtype of type $M_2$ of formula (II):
$A_2$ is O;
$R_6$ and $R_7$ are H; and
each $R_8$ is independently H or methyl.
In certain embodiments:
(a) for each monomer subtype of type $M_1$:
$A_1$ is O;
$R_1$ and $R_2$ are H; and
each $R_3$ is independently H or methyl;
(b) y is 1; and
(c) for $M_2$ of formula (II):
$A_2$ is O;
$R_6$ and $R_7$ are H; and
each $R_8$ is independently H or methyl.
In certain embodiments:
(a) x is 2;
(b) for each monomer subtype of type $M_1$:
$A_1$ is O;
$R_1$ and $R_2$ are H; and
each $R_3$ is independently H or methyl;
(c) y is 2; and
(d) for each monomer subtype of type $M_2$ of formula (II):
$A_2$ is O;
$R_6$ and $R_7$ are H; and
each $R_8$ is independently H or methyl.
In certain embodiments:
(a) x is 2;
(b) for each monomer subtype of type $M_1$:
$A_1$ is O;
$R_1$ and $R_2$ are H; and
each $R_3$ is independently H or methyl;
(c) y is 1; and
(d) for $M_2$ of formula (II):
$A_2$ is O;
$R_6$ and $R_7$ are H; and
each $R_8$ is independently H or methyl.

In certain embodiments:
(a) x is 1;
(b) for $M_1$:
  $A_1$ is O;
  $R_1$ and $R_2$ are H; and
  each $R_3$ is independently H or methyl;
(c) y is 2; and
(d) for each monomer subtype of type $M_2$ of formula (II):
  $A_2$ is O;
  $R_6$ and $R_7$ are H; and
  each $R_8$ is independently H or methyl.

In certain embodiments:
(a) x is 1;
(b) for $M_1$:
  $A_1$ is O;
  $R_1$ and $R_2$ are H; and
  each $R_3$ is independently H or methyl;
(c) y is 1; and
(d) for $M_2$ of formula (II):
  $A_2$ is O;
  $R_6$ and $R_7$ are H; and
  each $R_8$ is independently H or methyl.

In some embodiments, a composition of the invention is free of crosslinked polymers. In some embodiments, a composition of the invention is substantially free of crosslinked polymers.

In some embodiments, $M_1$, or each monomer subtype of type $M_1$ if x>1, is N-vinylformamide, N-vinylacetamide, N-vinylpropamide, N-vinylbutamide, N-vinylpentamide, N-vinylhexamide, N-vinylheptamide, N-vinyloctamide, N-vinylnonamide, N-vinyldecamide, N-methyl-N-vinylformamide, N-methyl-N-vinylacetamide, N-methyl-N-vinylpropamide, N-methyl-N-vinylbutamide, N-methyl-N-vinylpentamide, N-methyl-N-vinylhexamide, N-methyl-N-vinylheptamide, N-methyl-N-vinyloctamide, N-methyl-N-vinylnonamide, N-methyl-N-vinyldecamide, N-ethyl-N-vinylformamide, N-ethyl-N-vinylacetamide, N-ethyl-N-vinylpropamide, N-ethyl-N-vinylbutamide, N-ethyl-N-vinylpentamide, N-ethyl-N-vinylhexamide, N-ethyl-N-vinylheptamide, N-ethyl-N-vinyloctamide, N-ethyl-N-vinylnonamide, N-ethyl-N-vinyldecamide, N-n-propyl-N-vinylformamide, N-n-propyl-N-vinylacetamide, N-n-propyl-N-vinylpropamide, N-n-propyl-N-vinylbutamide, N-n-propyl-N-vinylpentamide, N-n-propyl-N-vinylhexamide, N-n-propyl-N-vinylheptamide, N-n-propyl-N-vinyloctamide, N-n-propyl-N-vinylnonamide, N-n-propyl-N-vinyldecamide, N-iso-propyl-N-vinylformamide, N-iso-propyl-N-vinylacetamide, N-iso-propyl-N-vinylpropamide, N-iso-propyl-N-vinylbutamide, N-iso-propyl-N-vinylpentamide, N-iso-propyl-N-vinylhexamide, N-iso-propyl-N-vinylheptamide, N-iso-propyl-N-vinyloctamide, N-iso-propyl-N-vinylnonamide, N-iso-propyl-N-vinyldecamide, or a mixture thereof.

In some embodiments, $M_1$, or each monomer subtype of type $M_1$ if x>1, is N-vinylformamide, N-vinylpropamide, N-vinylbutamide, N-vinylpentamide, N-vinylhexamide, N-vinylheptamide, N-vinyloctamide, N-vinylnonamide, N-vinyldecamide, N-methyl-N-vinylformamide, N-methyl-N-vinylacetamide, N-methyl-N-vinylpropamide, N-methyl-N-vinylbutamide, N-methyl-N-vinylpentamide, N-methyl-N-vinylhexamide, N-methyl-N-vinylheptamide, N-methyl-N-vinyloctamide, N-methyl-N-vinylnonamide, N-methyl-N-vinyldecamide, N-ethyl-N-vinylformamide, N-ethyl-N-vinylacetamide, N-ethyl-N-vinylpropamide, N-ethyl-N-vinylbutamide, N-ethyl-N-vinylpentamide, N-ethyl-N-vinylhexamide, N-ethyl-N-vinylheptamide, N-ethyl-N-vinyloctamide, N-ethyl-N-vinylnonamide, N-ethyl-N-vinyldecamide, N-n-propyl-N-vinylformamide, N-n-propyl-N-vinylacetamide, N-n-propyl-N-vinylpropamide, N-n-propyl-N-vinylbutamide, N-n-propyl-N-vinylpentamide, N-n-propyl-N-vinylhexamide, N-n-propyl-N-vinylheptamide, N-n-propyl-N-vinyloctamide, N-n-propyl-N-vinylnonamide, N-n-propyl-N-vinyldecamide, N-iso-propyl-N-vinylformamide, N-iso-propyl-N-vinylacetamide, N-iso-propyl-N-vinylpropamide, N-iso-propyl-N-vinylbutamide, N-iso-propyl-N-vinylpentamide, N-iso-propyl-N-vinylhexamide, N-iso-propyl-N-vinylheptamide, N-iso-propyl-N-vinyloctamide, N-iso-propyl-N-vinylnonamide, N-iso-propyl-N-vinyldecamide, or a mixture thereof.

In some embodiments, y is 0 and $M_1$, or each monomer subtype of type $M_1$ if x>1, is N-vinylhexamide, N-vinylheptamide, N-vinyloctamide, N-vinylnonamide, N-vinyldecamide, N-methyl-N-vinylformamide, N-methyl-N-vinylacetamide, N-methyl-N-vinylpropamide, N-methyl-N-vinylbutamide, N-methyl-N-vinylpentamide, N-methyl-N-vinylhexamide, N-methyl-N-vinylheptamide, N-methyl-N-vinyloctamide, N-methyl-N-vinylnonamide, N-methyl-N-vinyldecamide, N-ethyl-N-vinylformamide, N-ethyl-N-vinylacetamide, N-ethyl-N-vinylpropamide, N-ethyl-N-vinylbutamide, N-ethyl-N-vinylpentamide, N-ethyl-N-vinylhexamide, N-ethyl-N-vinylheptamide, N-ethyl-N-vinyloctamide, N-ethyl-N-vinylnonamide, N-ethyl-N-vinyldecamide, N-n-propyl-N-vinylformamide, N-n-propyl-N-vinylacetamide, N-n-propyl-N-vinylpropamide, N-n-propyl-N-vinylbutamide, N-n-propyl-N-vinylpentamide, N-n-propyl-N-vinylhexamide, N-n-propyl-N-vinylheptamide, N-n-propyl-N-vinyloctamide, N-n-propyl-N-vinylnonamide, N-n-propyl-N-vinyldecamide, N-iso-propyl-N-vinylformamide, N-iso-propyl-N-vinylacetamide, N-iso-propyl-N-vinylpropamide, N-iso-propyl-N-vinylbutamide, N-iso-propyl-N-vinylpentamide, N-iso-propyl-N-vinylhexamide, N-iso-propyl-N-vinylheptamide, N-iso-propyl-N-vinyloctamide, N-iso-propyl-N-vinylnonamide, N-iso-propyl-N-vinyldecamide, or a mixture thereof.

In some embodiments, $M_1$, or each monomer subtype of type $M_1$ if x>1, is N-vinylformamide, N-vinylacetamide, N-vinylpropamide, N-vinylbutamide, N-methyl-N-vinylformamide, N-methyl-N-vinylacetamide, N-methyl-N-vinylpropamide, N-methyl-N-vinylbutamide, N-ethyl-N-vinylformamide, N-ethyl-N-vinylacetamide, N-ethyl-N-vinylpropamide, N-ethyl-N-vinylbutamide, N-n-propyl-N-vinylformamide, N-n-propyl-N-vinylacetamide, N-n-propyl-N-vinylpropamide, N-n-propyl-N-vinylbutamide, N-iso-propyl-N-vinylformamide, N-iso-propyl-N-vinylacetamide, N-iso-propyl-N-vinylpropamide, N-iso-propyl-N-vinylbutamide, or a mixture thereof.

In other embodiments, $M_2$, or each monomer subtype of type $M_2$ if y>1, is one of the groups set forth in Section 4.1 of the Detailed Description of the Invention. In other embodiments, in each of such embodiments for $M_2$, each $M_1$, or each monomer subtype of type $M_1$ if x>1, is independently N-vinylformamide, N-vinylacetamide or N-methyl-N-vinylacetamide or, alternatively, each $M_1$, or each monomer subtype of type $M_1$ if x>1, is independently N-vinylformamide or N-methyl-N-vinylacetamide.

In other embodiments, the polymer of the invention is a copolymer that is poly(N-vinylformamide-co-acrylamide); poly(N-vinylformamide-co-N-methyl-acrylamide); poly(N-vinylformamide-co-N,N-dimethyl-acrylamide); poly(N-vinylformamide-co-N-methoxymethyl-acrylamide); poly(N-vinylformamide-co-N-2-hydroxyethyl-acrylamide); poly (N-vinylformamide-co-methacrylamide); poly(N-vinylformamide-co-N-methyl-methacrylamide); poly(N-vinylformamide-co-N,N-dimethyl-methacrylamide); poly (N-vinylformamide-co-N-methoxymethyl-methacrylamide); poly(N-vinylformamide-co-N-2-hydroxyethyl-methacrylamide); poly(N-vinylformamide-co-1-vinyl-pyrrolidine-2,5-dione); poly(N-vinylformamide-co-vinyl acetate); poly(N-vinylformamide-co-vinyl acetate-co-vinyl alcohol); poly(N-vinylacetamide-co-acrylamide); poly(N-vinylacetamide-co-N-methyl-acrylamide); poly(N-vinylacetamide-co-N,N-dimethyl-acrylamide); poly(N-vinylacetamide-co-N-methoxymethyl-acrylamide); poly(N-vinylacetamide-co-N-2-hydroxyethyl-acrylamide); poly(N-vinylacetamide-co-methacrylamide); poly(N-vinylacetamide-co-N-methyl-methacrylamide); poly(N-vinylacetamide-co-N,N-dimethyl-methacrylamide); poly(N-vinylacetamide-co-N-methoxymethyl-methacrylamide); poly(N-vinylacetamide-co-N-2-hydroxyethyl-methacrylamide); poly(N-vinylacetamide-co-1-vinyl-pyrrolidine-2,5-dione); poly(N-vinylacetamide-co-vinyl acetate); poly(N-vinylacetamide-co-vinyl acetate-co-vinyl alcohol); poly(N-methyl-N-vinylacetamide-co-acrylamide); poly(N-methyl-N-vinylacetamide-co-N-methyl-acrylamide); poly(N-methyl-N-vinylacetamide-co-N,N-dimethyl-acrylamide); poly(N-methyl-N-vinylacetamide-co-N-methoxymethyl-acrylamide); poly(N-methyl-N-vinylacetamide-co-N-2-hydroxyethyl-acrylamide); poly(N-methyl-N-vinylacetamide-co-methacrylamide); poly(N-methyl-N-vinylacetamide-co-N-methyl-methacrylamide); poly(N-methyl-N-vinylacetamide-co-N,N-dimethyl-methacrylamide); poly(N-methyl-N-vinylacetamide-co-N-methoxymethyl-methacrylamide); poly(N-methyl-N-vinylacetamide-co-N-2-hydroxyethyl-methacrylamide); poly(N-methyl-N-vinylacetamide-co-1-vinyl-pyrrolidine-2,5-dione); poly(N-methyl-N-vinylacetamide-co-vinyl acetate); poly(N-methyl-N-vinylacetamide-co-vinyl acetate-co-vinyl alcohol); or salts thereof.

In other embodiments, the polymer of the invention is a copolymer that is poly(N-vinylformamide-co-acrylamide); poly(N-vinylformamide-co-N,N-dimethyl-acrylamide); poly(N-vinylformamide-co-N-methoxymethyl-acrylamide); poly(N-vinylformamide-co-methacrylamide); poly(N-vinylformamide-co-N,N-dimethyl-methacrylamide); poly(N-vinylformamide-co-N-methoxymethyl-methacrylamide); poly(N-vinylformamide-co-1-vinyl-pyrrolidine-2,5-dione); poly(N-vinylformamide-co-vinyl acetate); poly(N-methyl-N-vinylacetamide-co-acrylamide); poly(N-methyl-N-vinylacetamide-co-N,N-dimethyl-acrylamide); poly(N-methyl-N-vinylacetamide-co-N-methoxymethyl-acrylamide); poly(N-methyl-N-vinylacetamide-co-methacrylamide); poly(N-methyl-N-vinylacetamide-co-N,N-dimethyl-methacrylamide); poly(N-methyl-N-vinylacetamide-co-N-methoxymethyl-methacrylamide); poly(N-methyl-N-vinylacetamide-co-1-vinyl-pyrrolidine-2,5-dione); poly(N-methyl-N-vinylacetamide-co-vinyl acetate); or salts thereof.

In some embodiments, compositions of the invention can suppress or eliminate electroosmosis or electroosmotic flow ("EOF"), which refers to capillary-fluid flow induced by an electrical field. In addition, compositions of the invention can provide excellent electrophoretic resolution.

In some embodiments, compositions of the invention comprise an effective amount of a polymer of the invention. For the purposes of this application, an "effective amount of a polymer of the invention" means that the polymer is present in an amount or concentration sufficient to separate a biomolecule from at least one other molecule, e.g., an amount effective to cause at least two biomolecule components of a sample mixture to have different mobilities in CE. The weight fraction of a polymer of the invention present in a composition of the invention, based on the total weight of composition, is from about 0.0001 to about 0.02. In another embodiment, the weight fraction of the polymer of the invention present in a composition of the invention is from about 0.001 to about 0.015. In another embodiment, the weight fraction of the polymer of the invention present in a composition of the invention is from about 0.001 to about 0.005.

4.3.1. Buffer

The present compositions comprise a buffer for controlling pH. In one embodiment, the buffer is an aqueous buffer.

In another embodiment, the buffer is a substantially dry buffer. In another embodiment, the buffer is a dry buffer. In another embodiment, the buffer provides a buffered composition with a pH of from about 5 to about 11. In another embodiment, the buffer provides a buffered composition with a pH of from about 7 to about 10. Exemplary aqueous buffers include aqueous solutions of organic acids, such as citric, acetic or formic acid; zwitterionics, such as N-tris (hydroxymethyl)-2-aminoethane sulfonic acid ("TES"), N,N-bis-(2-hydroxyethyl)glycine ("BICINE"), 2-(2-amino-2-oxoethyl)-amino)ethane sulfonic acid ("ACES") or glycylglycine; inorganic acids, such as phosphoric acid; and organic bases, such as TRIS. Exemplary substantially dry buffers can be prepared from each of the above aqueous buffers by substantially evaporating the water. Exemplary dry buffers can be prepared from each of the above aqueous buffers by completely evaporating the water.

Buffer concentration can vary widely, for example from about 1 mmol to about 1 mol, and often about 20 mmol/liter of water is used. Exemplary buffer solutions for conventional CE applications include the following: 0.1 M TRIS, 0.25 M boric acid, 7 M urea with a pH of about 7.6 for single stranded polynucleotide separations; or 0.089 M TRIS, 0.089 M boric acid, 0.005 M ethylenediamine tetraacetic acid ("EDTA") for double stranded polynucleotide separations.

In another embodiment, the buffers include "GA" buffer, "TTE" buffer, or a mixture thereof. GA buffer comprises 3-((2-hydroxy-1,1-bis-(hydroxymethyl)ethyl))-amino)-1-propanesulfonic acid sodium salt ("TAPS") and EDTA with from about 1 to about 4 mM of EDTA present per 100 mM of TAPS such that the pH of the buffer is about 8.0. In another embodiment, the GA buffer can be used in a concentrated form, i.e., 10×GA buffer, which comprises from about 10 to about 40 mM of EDTA present per 100 mM of TAPS. TTE buffer comprises TRIS, TAPS and EDTA with about 1 mM of EDTA present per 50 mM of TRIS plus 50 mM of TAPS such that the pH of the buffer is about 8.4. In another embodiment, the TTE buffer can be used in a concentrated form, i.e., 10×TTE buffer, which comprises about 10 mM of EDTA present per 500 mM of TRIS plus 500 mM of TAPS.

An effective concentration of aqueous buffer present in a composition of the invention is from about 10 mM to about 300 mM. In one embodiment, the effective concentration of aqueous buffer is from about 25 mM to about 200 mM. In another embodiment, the concentration of aqueous buffer present in a composition of the invention is from about 50 mM to about 100 mM.

In another embodiment, an aqueous composition of the invention is uncrosslinked. In another embodiment, an aqueous composition of the invention is substantially uncrosslinked.

4.3.2. Sieve and/or EOF Suppressing Polymer

In some embodiments, for CE, compositions of the invention can provide useful sieving and/or EOF suppression functions to facilitate the separations of biomolecules such as polynucleotides. Whether a composition of the invention provides sieving or EOF suppression or both will depend on the amount or concentration of polymer that is present, whether a plurality of polymers are present and their relative amounts or concentrations, and other factors. For example, use of a polymer of the invention at a low concentration may be effective to suppress EOF but may not provide significant sieving. However, another polymer, i.e., a sieve and/or EOF suppressing polymer, can be included to provide a sieving function. Alternatively, a polymer of the invention can provide a sieving function but another polymer, i.e., a sieve and/or EOF suppressing polymer, can be included, usually at a smaller concentration, to suppress EOF if so desired. In yet another example, two or more polymers can be included in a composition of the invention (including at least one polymer of the invention) and the polymers can contribute to sieving, or to EOF suppression, or to both. For example, two different polymers may be present, each at a concentration that alone is insufficient for significant sieving, but such that the sum of the two polymers together provide a desired level of sieving. In yet another example, a single polymer of the invention provides both sieving and EOF suppression that is adequate for a particular electrophoretic separation.

In one embodiment, when present, the sieve and/or EOF suppressing polymer at least one of the dynamic, static or hybrid polymer wall coatings for CE. For example, those polymers and copolymers disclosed in J. Horvath et al., *Electrophoresis,* 22:644-655 (2001), can be used, such as poly(n-undecyl-α-D-glucopyranoside) (PUG), polyoxyethylene ether (BRIJ-35®), poly(dimethyldiallylammonium chloride) (PDMAC), poly(ethyleneimine) (PEI), polybrene (PB), poly(arginine) (PA), dextran, cationiccylodextran, 40-140 nm polystyrene particles derivatized with α-ω diamines, 40-140 nm polystyrene particles derivatized with α-ω diamines wherein the amino functionality is derivatized with 2,3-epoxy-1-propanol, poly(vinyl alcohol) (PVA), alkylene-glycol polymers, poly(N-vinylpyrrolidone) (PVP), copolymers of vinylpyrrolidone and vinylimidazole, poly (ethylene oxide) (PEO), (polyethylene oxide-polypropylene oxide-polyethylene oxide) triblock copolymer, poly(N-isopropyl acrylamide)-g-poly(ethylene oxide), poly(acrylamide), cross-linked polyacrylamide (acrylamide+bisacrylamide), poly(acrylamide-co-allyl α-D-glucopyranoside) (poly (AG-AA)), poly(acrylamide-co-allyl α-D-glucopyranoside-co-allylglycidyl ether) (epoxypoly(AG-AA)), poly(N,N'-dimethylacrylamide) (PDMA), copolymers of N,N'-dimethylacrylamide, such as poly(N,N'-dimethylacrylamide-co-allylglycidyl ether) (EPPDMA), graft copolymers of N,N'-dimethylacrylamide, poly(N-acryloyl aminoethoxyethanol) (polyAAEE), poly(N-acryloylaminopropanol) (polyAAP), poly(acryloyldiethanolamine), poly(2-aminoethyl methacrylate hydrochloride) (PALM), hydrophilic poly(ethylene glycol) (PEG), polyamide resin, polyamine (i.e., eCAP®), poly(vinylamine), sodium-2-acrylamido-2-methylpropanesulfonate (NaAMPS), fibrinogen, cellulose acetate, cellulose triacetate, methylcellulose (MC), hydroxypropylmethlylcellulose, hydroxyethylcellulose (HEC), cross-linked hydroxypropylcellulose (HPC), epoxybutane-modified hydroxyproplylcellulose (EB-HPC), and a copolymer of HPC and 2-hydroxyethyl methacrylate.

Optionally, in some embodiments, compositions of the invention can additionally comprise one or more sieve polymers, present in an effective amount. Without being bound by theory, a primary CE separation mechanism for different sized biomolecules, e.g., polynucleotides, is determined by their charge-to-frictional drag ratio. Thus, it is desirable that a sieve polymer is present if, in the absence of the same, two or more biomolecules would co-migrate in CE, i.e., move with about the same mobility. For the purposes of this application, an "effective amount of a sieve polymer" an "effective amount of an EOF suppressing polymer" and an "effective amount of a sieve and/or EOF suppressing polymer" means an amount effective to cause at least two biomolecule components of a sample mixture to have different mobilities in CE.

In some embodiments, compositions of the invention contain gelled or crosslinked polymers that provide sieving and/or EOF suppression properties. In other embodiments, compositions of the invention contain non-covalently-cross-linked sieve and/or EOF suppressing polymers comprising any or all of hydroxyalkylcellulose, agarose, cellulose acetate, linear polyacrylamide ("PAAm") and the like, as disclosed by, e.g., Bode, *Anal. Biochem.*, 83:204-210 (1977); Bode, *Anal. Biochem.*, 83:364-371 (1977); Bode, *Anal. Biochem.*, 92:99-110 (1979); Hjerten et al., *J. Liquid Chromatography*, 12:2471-2477 (1989); U.S. Pat. No. 5,126,021 to Grossman; and Tietz et al., *Electrophoresis*, 13:614-616 (1992).

In some embodiments, when present in the compositions of the invention, the sieve and/or EOF suppressing polymer is one or more substantially uncrosslinked polymers. In another embodiment, the sieve and/or EOF suppressing polymer is one or more substantially linear polymers.

In another embodiment, the sieve and/or EOF suppressing polymer is water soluble at atmospheric pressure, a concentration of from about 0.01 to about 1 wt. %, and from about 20° C. to about 70° C. In another embodiment, the sieve and/or EOF suppressing polymer is water soluble at atmospheric pressure, a concentration of from about 0.01 to about 1 wt. %, and at about 25° C.

In one embodiment, when a sieve and/or EOF suppressing polymer is present in the compositions of the invention, the sieve and/or EOF suppressing polymer has an Mw of from about 100,000 Da to about 5 MDa. In another embodiment, the sieve and/or EOF suppressing polymer has an Mw of from about 500,000 Da to about 2 MDa. In another embodiment, the sieve and/or EOF suppressing polymer, when present, has an Mw of from about 800,000 Da to about 2 MDa.

In one embodiment, the sieve and/or EOF suppressing polymer comprises a monomer unit that is acrylamide, N-acetyl-acrylamide, N-2-cyanoethyl-acrylamide, N,N-1,2-dihydroxyethylene-bis-acrylamide, N-4,4-dimethoxybutyl-acrylamide, N-2,2-dimethoxyethyl-acrylamide, N,N-dimethyl-acrylamide, N-2-glycolic acid methyl ester acrylamide, N-2-hydroxyethyl-acrylamide, N-hydroxymethyl-acrylamide, N-methoxymethyl-acrylamide, N-3-methoxypropyl-acrylamide, N-methyl-acrylamide, N-methyl-, N-2,2-dimethoxyethyl-acrylamide, N-morpholinoethyl-acrylamide, N-2,2,2-trichloro-1-hydroxyethyl-acrylamide, N-tri(hydroxymethyl)-methyl-acrylamide, methacrylamide, N-acetyl-methacrylamide, N-2-cyanoethyl-methacrylamide, N,N-1,2-dihydroxyethylene-bis-methacrylamide, N-4,4-dimethoxybutyl-methacrylamide, N-2,2-dimethoxyethyl-methacrylamide, N,N-dimethyl-methacrylamide, N-2-glycolic acid methyl ester methacrylamide, N-2-hydroxyethyl-methacrylamide, N-hydroxymethyl-methacrylamide, N-methoxymethyl-methacrylamide, N-3-methoxypropyl-methacrylamide, N-methyl-methacrylamide, N-methyl-, N-2,2-dimethoxyethyl-methacrylamide, N-morpholinoethyl-methacrylamide, N-2,2,2-trichloro-1-hydroxyethyl-methacrylamide, or N-tri(hydroxymethyl)-methyl-methacrylamide, or a mixture thereof.

In another embodiment, the sieve and/or EOF suppressing polymer is poly(hydroxymethylene), poly(oxyethylene), poly(oxypropylene), poly(oxyethylene-co-oxypropylene), poly(vinyl alcohol), poly(vinylpyrrolidone), poly(2-ethyl-2-oxazoline), poly(2-methyl-2-oxazoline), poly ((2-ethyl-2-oxazoline)-co-(2-methyl-2-oxazoline)), poly(N-acetamido-acrylamide), poly(acryloxylurea), a water-soluble polysaccharide such as hydroxyethyl cellulose or hydroxymethyl cellulose, or a mixture thereof.

In one embodiment, the sieve and/or EOF suppressing polymer includes an acrylamide monomer unit. In another embodiment, at least about 80 mol % of the sieve and/or EOF suppressing polymer's monomer units are acrylamide units. In another embodiment, at least about 90 mol % of the sieve and/or EOF suppressing polymer's monomer units are acrylamide units. In another embodiment, at least about 95 mol % of the sieve and/or EOF suppressing polymer's monomer units are acrylamide units. In another embodiment, the sieve and/or EOF suppressing polymer is polyacrylamide that is substantially linear, i.e., in which the amount of branching is insignificant such that the solution viscosity of that polyacrylamide is not substantially different from the solution viscosity of a substantially linear polyacrylamide having the same Mw.

When present, the weight fraction of sieve and/or EOF suppressing polymer in a composition of the invention, based on the total weight of the composition, is from about 0.001 to about 0.1. In another embodiment, the weight fraction of sieve and/or EOF suppressing polymer in a composition of the invention is from about 0.005 to about 0.05. In another embodiment, the weight fraction of sieve and/or EOF suppressing polymer present in a composition of the invention is from about 0.01 to about 0.03 (0.01 wt. fraction=1 wt. %).

4.3.3. Denaturant

Additional optional components, such as denaturants, can be included in the compositions of the invention, e.g., when it is desirable to prevent the formation of duplexes or secondary structures in polynucleotides. In one embodiment, denaturants include formamide, urea, detergents such as sodium dodecyl sulfate, and commercially available lactams, such as pyrrolidone and N-methyl pyrrolidone, as well as their mixtures. The use of denaturants in electrophoresis is conventional and is described in, e.g., recognized molecular biology references such as Sambrook et al., *Molecular Cloning: A Laboratory Manual*, (Cold Spring Harbor Laboratory, New York, $2^{nd}$ Ed. 1989). In another embodiment, the denaturanit, when present, is formamide, urea, pyrrolidone, N-methyl pyrrolidone, or a mixture thereof. In another embodiment, the denaturant, when present, is urea. In another embodiment, the denaturant, when present, is formamide.

When present, the concentration of denaturant in a composition of the invention is from about 0.5 M to about 8 M. In another embodiment, the concentration of denaturant is from about 2 M to about 8 M. In another embodiment, the concentration of denaturant present in a composition of the invention is from about 6 M to about 8 M.

4.4. Methods for Making Compositions

A fourth embodiment of the invention relates to a method for making a composition of the invention, comprising admixing a polymer of the invention with a buffer. This method can further comprise admixing with a sieve and/or EOF suppressing polymer or a salt thereof and/or a denaturant. The compositions of the invention are useful as electrophoresis separation media. For example, a composition of the invention can be prepared by dissolving, at 25° C., a polymer of the invention and, when it is present, the sieve and/or EOF suppressing polymer or salt thereof, in water followed by adding a concentrated form of the buffer. Alternatively, the polymer of the invention can be dissolved directly in an aqueous buffer and, optionally, a sieve and/or EOF suppressing polymer can be added to that solution. The denaturant can be present either before or after the optional sieve and/or EOF suppressing polymer is added. Thus, the polymer of the invention, and the sieve and/or EOF suppressing polymer when it is present, can be added to water, aqueous buffer, water and denaturant, or aqueous buffer and denaturant, depending on which combination is selected for use. Moreover, when the sieve and/or EOF suppressing polymer is present, it can be dissolved in, e.g., the buffer, before the polymer of the invention is introduced. Any order of adding the components for making a composition of the invention is within the scope of this embodiment of the invention.

4.5. Methods for Separating

In a fifth embodiment of the invention, the compositions of the invention are useful in a method for detecting or separating a sample or analyte, e.g., a biomolecule or mixture of biomolecules. As used herein, "analyte" includes the substance for which a particular sample is being tested, e.g., for the presence and/or amount contained in the sample.

For example, a suitable method for separating a mixture of biomolecules using a composition of the invention comprises:
(a) contacting a composition of the invention with a mixture comprising a biomolecule; and
(b) applying an electric field to the composition in an amount sufficient to facilitate the separation of a biomolecule from the mixture.

In another embodiment, the composition of the invention further comprises a sieve and/or EOF suppressing polymer or a salt thereof. In another embodiment, the composition of the invention further comprises a denaturant. In another embodiment, the composition of the invention is in a support such as a capillary tube or column, prior to contacting with a biomolecule.

The biomolecule(s) can be a polynucleotide or polynucleotides. In one embodiment, biomolecules include proteins, glycoproteins, natural and synthetic peptides, alkaloids, polysaccharides, polynucleotides, and the like. In another embodiment, biomolecule refers to polynucleotides. In another embodiment, a biomolecule can be a polysaccharide. In another embodiment, a biomolecule can be a negatively-charged polysaccharide. In another embodiment, a biomolecule can be a carbohydrate. In another embodiment, a biomolecule can be a negatively-charged carbohydrate. In another embodiment, biomolecules can be a mixture comprising a polynucleotide, a polysaccharide and a carbohydrate. In another embodiment, biomolecules can be a mixture comprising a polynucleotide and a carbohydrate. In another embodiment, biomolecules can be a mixture comprising a polynucleotide and a polysaccharide. In another embodiment, biomolecules can be a mixture comprising a polysaccharide and a carbohydrate.

The term "polynucleotide," as used herein, refers to a linear polymer of natural or modified nucleoside monomers, including double and single stranded deoxyribonucleosides, ribonucleosides, α-anomeric forms thereof, and the like. Usually the nucleoside monomers are linked by phosphodiester bonds or analogs thereof to form polynucleotides ranging in size from a few monomeric units, e.g., from about 8 to about 40, to several thousands of monomeric units. Whenever a polynucleotide is represented by a sequence of letters, such as "GTTACTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoroselenoate, phosphorodiselenoate, phosphoroanilothioate, phosphoranilidate, phosphoramidate, and the like.

As used herein, "nucleoside" includes the natural nucleosides, including 2'-deoxy and 2'-hydroxyl forms, e.g., as described in Kornberg and Baker, *DNA Replication*, 2nd Ed. (Freeman, San Francisco, 1992). "Analogs" in reference to nucleosides includes synthetic nucleosides having modified base moieties and/or modified sugar moieties, e.g., described generally by Scheit, *Nucleotide Analogs* (John Wiley, New York, 1980).

Regarding the degree of separation of a sample or analyte, it is conventional in CE that "resolution" or "Rs" is defined as:

$$Rs=0.59(Y_2-Y_1)/FWHM \qquad (1)$$

where $Y_1$ and $Y_2$ are the centers of two adjacent CE peaks and FWHM is the peak width at half-height, assuming that both peaks have substantially the same width. (See, e.g., Albarghouthi, *Electrophoresis*, 21:4096-4111 (2000)). As used herein, "crossover" is the number of base pairs for the base pair whose $(Y_2-Y_1)$ value is equal to its FWHM value. In other words, a crossover of 650 base pairs ("bp") means that the resolution of the $650^{th}$ base pair is 0.59.

In one embodiment, in a method for separating a mixture of biomolecules using a composition of the invention, the method results in a crossover of at least 400 bp. In another embodiment, in a method for separating a mixture of biomolecules using a composition of the invention, the method results in a crossover of at least about 600 bp. In another embodiment, in a method for separating a mixture of biomolecules using a composition of the invention, the method results in a crossover of at least about 700 bp. In another embodiment, in a method for separating a mixture of biomolecules using a composition of the invention, the method results in a crossover of at least about 800 bp. In another embodiment, in a method for separating a mixture of biomolecules using a composition of the invention, the method results in a crossover of at least about 900 bp. In another embodiment, in a method for separating a mixture of biomolecules using a composition of the invention, the method results in a crossover of at least about 1000 bp. In another embodiment, in a method for separating a mixture of biomolecules using a composition of the invention, the method results in a crossover of at least about 1100 bp. In another embodiment, in a method for separating a mixture of biomolecules using a composition of the invention, the method results in a crossover of at least about 1200 bp.

4.6. Electrophoresis Apparatus

An electrophoresis apparatus comprises a support, e.g., a capillary, for a composition of the invention. In one embodiment, the support defines an elongate channel connectable at opposite ends to opposing polarity terminals of a voltage source for containing a composition of the invention, e.g., a separation medium. The term "capillary," as used herein, refers to a tube or channel or other structure capable of supporting a volume of composition of the invention useful for carrying out electrophoresis. The geometry of a support or capillary can vary widely and includes tubes with circular, rectangular or square cross-sections, channels, groves, plates and the like, each of which can be fabricated by a wide range of technologies. For example, the support can comprise a CE array of bundled capillary channels. Alternately, the support can be of the microfabricated type, such as a channel chemically etched into a glass wafer as described by, e.g., Liu et al., *Anal. Chem.*, 71:566-573 (1999). Exemplary references describing CE microchip apparatuses include the previous citation and Woolley et al., *Anal. Chem.*, 67:3676-3680 (1995), which discloses a CE microchip with a plurality of support channels, each measuring 50 μm wide and 8 μm deep.

An important feature of a support used with the composition of the invention is the surface area-to-volume ratio of the support's inner surface that is in contact with the volume of the composition of the invention. High values of this ratio permit better heat transfer from the composition during electrophoresis. In one embodiment, values in the range of from about 20,000 to about 200,000 are employed. These correspond to the surface area-to-volume ratios of tubular capillaries with circular cross-sections having inside diameters of from about 200 µm to about 10 µm.

In another embodiment, the support is a tubular capillary having a length of from about 10 to about 200 cm. In another embodiment, the support is a tubular capillary having a length of less than about 100 cm. In another embodiment, the support is a tubular capillary having an inner diameter of from about 10 to about 200 µm. In another embodiment, the support is a tubular capillary having an inner diameter of from about 25 to about 75 µm.

Capillaries for the invention can be made of silica, fused silica, silicate-based glass, such as borosilicate glass, alumina-containing glass, phosphate glass, quartz and the like, or other silica-like materials. In one embodiment, the capillary comprises fused silica. The capillary can be uncoated on its outside surface. In another embodiment, the capillary is coated on the outside surface with a polyimide layer, e.g., to provide sufficient mechanical strengthening and/or promote ease of handling. The capillary can be coated on its inside surface, with one or a plurality of layers, typically with a silane-derived coating and/or PAAm as described in, e.g., U.S. Pat. No. 4,997,537 to Karger et al., at col. 5, line 9 to col. 6, line 14. In another embodiment, the capillary is uncoated on the inside surface.

Apparatuses for performing capillary electrophoresis are well-known. Several CE instruments are commercially available, e.g., the Applied Biosystems Inc. (ABI, Foster City, Calif.) model 310 Genetic Analyzer, models 3700 and 3730 DNA Analyzer, and the ABI PRISM® 3100 Genetic Analyzer. Exemplary references describing CE apparatus and their operation include Colburn et al., *Applied Biosystems Research News*, Issue 1 (Winter 1990); Grossman et al., Eds., *Capillary Electrophoresis* (Academic Press, San Diego, 1992); Harrison et al., *Science,* 261:895-897 (1993); U.S. Pat. No. 4,908,112 to Pace; U.S. Pat. No. 5,192,412 to Kambara et al.; and Seiler et al., *Anal. Chem.,* 65:1481-1488 (1993).

Contacting a composition of the invention with the support such that the support contains the composition can be performed using conventional methods, e.g., by connecting one end to a syringe and injecting the composition into the support under a controlled pressure. When the support is a capillary, the injection pressure can range from about 50 to about 800 psi. In another embodiment, the injection pressure for the capillary support is from about 200 to about 400 psi. Alternately, contacting a composition of the invention with the support such that the support contains the composition can be performed by connecting the capillary support to a filling tube and applying a nitrogen or helium gas pressure of from about 100 to about 500 psi for from about 5 to about 60 minutes, depending on the viscosity of the composition. U.S. Pat. No. 4,997,537 to Karger et al. discloses PAAm filling with a TEFLON tube and a syringe.

Another way for introducing a composition to the support so that the composition is contained therein is by immersing one of the two ends of the support into a reservoir containing a composition of the invention and increasing the air pressure above that composition to greater than atmospheric pressure, thereby forcing the composition into the support via positive pressure. Alternatively, the air pressure at the end of the support opposite to its immersed end can be reduced to below atmospheric, thereby drawing the composition into the support by suction.

Regardless of the method used, it is known in the art that the contained composition should fill the support substantially uniformly and homogeneously, i.e., the composition should be substantially uniform in density throughout the support and be substantially without discontinuities or voids. See, e.g., U.S. Pat. No. 5,468,365 to Menchen et al., col. 16, lines 33-45. The Brookfield viscosity of a composition of the invention is suitably from about 100 to about 1000 cPs. In another embodiment, the Brookfield viscosity of a composition of the invention is from about 200 to about 500 cPs. The compositions of the invention are appropriately characterized by Method A of the ASTM D 2196-99 test entitled "Standard Test Methods for Rheological Properties of Non-Newtonian Materials by Rotational (Brookfield type) Viscometer." In this test and by "Method A" described therein, the apparent or Brookfield viscosity is determined by experimentally measuring the torque on a spindle rotating at a constant speed within the liquid composition at a temperature of 25° C. Spindle No. 00 is used at a rotational speed of 10 rpm in a Brookfield Model RV Viscometer or its equivalent for all of these experiments.

A sixth embodiment of the invention relates to a support containing a composition of the invention. In another embodiment, the support is a capillary. In another embodiment, the capillary is a capillary tube.

In another embodiment, when multiple CE runs are conducted for a given composition/analyte combination, the composition is substantially removed, i.e., 99%, removed from the capillary at the completion of each CE run and a fresh aliquot of the composition is introduced before the start of the next CE run. In another embodiment, the entire removal and filling operation is conducted under automatic control, e.g., to promote reliable and reproducible CE results.

A cathodic reservoir can contain the composition into which a cathode and the cathodic end of the capillary are immersed during electrophoresis, except for the brief period of time in which the sample is added. The air pressure above the composition can be controlled, e.g., for loading the composition into the capillary by positive pressure. An anodic reservoir can contain the composition into which an anode and the anodic end of the capillary is immersed during electrophoresis. The air pressure above that portion of the composition can also be controlled, if desired e.g., for drawing the composition into the capillary under reduced pressure. In another embodiment, the composition in the cathodic reservoir is about the same as the composition in the anodic reservoir. The entire CE apparatus is maintained at a preselected constant temperature throughout a separation run.

A high-voltage source is connected between the cathode and anode such that a run potential in the range of from about 2 to about 60 kV is produced across the electrodes throughout CE. In another embodiment, the potential is in the range of from about 5 to about 20 kV. Alternatively, or in addition, a selected-frequency pulsed voltage can be applied between the electrodes, if desired. Currents through the capillary during the CE run can be in the microamp range, typically from about 2 to about 100 µA. In another embodiment, currents through the capillary during the CE run are from about 5 to about 30 µA.

A sample or analyte to be analyzed using CE comprises a mixture of biomolecules. To begin a CE run, the sample and the composition of the invention can be contacted by any known means, e.g., by syringe layering injection or differential pressure. In another embodiment, the sample is added by electrokinetic injection, e.g., by placing the cathode and cathodic end of the capillary into a sample solution then applying an injection potential and current across the capillary for a short time. The sample can be electrokinetically injected for about 3 to about 150 seconds under a potential of from about 0.5 to about 18 kV. Separation can commence after returning the cathode and cathodic end of the capillary into the cathode reservoir and application of the run potential and current.

An on-line detector positioned adjacent to capillary and nearer to its anodic end monitors separated bands of sample migrating through a detection zone of the capillary. Typically, an optical detection zone comprises a region of capillary in which any outer coating has been removed to allow UV and/or visible light, e.g. fluorescence, detection of the separated analyte. However, a wide variety of detection schemes are can be used with the invention, including UV absorbance, fluorescence emission, laser-induced fluorescence, conductance, radioactive emission and the like. For example, detection systems for fluorescent analytes are described in U.S. Pat. No. 4,675,300 to Zare et al. and U.S. Pat. No. 4,548,498 to Folestad et al. Alternately, a 4-color detection system, such as is conventional in DNA analysis, utilizing an argon ion laser as a fluorescence-excitation light source that emits light at wavelengths of 488 and 514 nm used in conjunction with a charged coupled device detector has be described in U.S. Pat. No. 5,916,426 to Madabhushi et al.

Prior to its use with a different analyte and/or composition, the capillary can be flushed, e.g., with 20 column volumes of water, 20 column volumes tetrahydrofuran (THF), 20 column volumes 1 M NaOH and 20 column volumes of water, before a composition of the invention is added to it. In order to provide, e.g., reliable and reproducible CE results, in one embodiment the used capillary is replaced with an unused capillary containing fresh composition and the sample is added by electrokinetic injection, as described above.

5. EXAMPLES

As noted above, the polymer of the invention yield advantageous CE performance in the analysis and separation of biomolecules. The following examples further illustrate certain embodiments of the present invention. These examples are provided solely for illustrative purposes and in no way limit the scope of the present invention.

5.1. Preparation of Illustrative Compositions of the Invention Comprising PVF

A series of three compositions, $IC_1$-3, comprised poly(N-vinylformamide) ("PVF"). Each of these compositions also comprised poly(N,N-dimethylacrylamide) ("PDMA"). The weight percent for each of the components present in each composition is provided in Table 1.

TABLE 1

Illustrative Compositions of the Invention Comprising PVF

| Composition Designation | IC1 | IC2 | IC3 |
|---|---|---|---|
| PVF Mw | 2559 kDa | 1238 kDa | 1125 kDa |
| PVF Amount | 2.23% | 2.21% | 2.17% |
| 10X TTE Buffer Amount | 8.91% | 8.94% | 10.70% |
| Urea Amount | 37.88% | 38.02% | 37.21% |
| MILLI-Q Water Amount | 50.77% | 50.63% | 49.73% |
| PDMA$^a$ Amount | 0.21% | 0.20% | 0.20% |

$^a$Mw = 984 kDa, Mn = 315 kDa

Each of IC1-IC3 was prepared using substantially linear PDMA of Mw about 984 kDa and Mn about 315 kDa, as determined by GPC-MALLS, that was dialyzed and lyophilized prior to its use. PDMA was also included to reduce EOF. The PDMA was dialyzed with 50K MWCO Spectra/Por-7 regenerated cellulose membranes for 4 days with two changes of water (5 gallons each) and lyophilized prior to its use. The water used in each of IC1-3 was purified using a MILLI-Q Water System (Millipore Corp., Bedford, Mass.).

The Brookfield viscosity of each composition, as measured by Method A of the ASTM D 2196-99 test discussed above, ranged from about 300 to about 500 centipoise. It was observed that, in general, the lower the molecular weight of the PVF used, the lower was the viscosity of the composition.

5.2. Capillary Electrophoresis of DNA Using Compositions Comprising PVF

Compositions comprising an illustrative polymer of the invention were evaluated for their usefulness as capillary electrophoresis separation media in DNA sequencing. In the following examples, each composition of the invention was evaluated in CE by using an ABI 310 Genetic Analyzer equipped with a 47 cm long by 50 μm inner diameter uncoated fused silica capillary.

In each comparative separation medium ("CSM") "control," either GA buffer or TTE buffer was used. Urea denaturant was also present. Each separation medium was prepared by dissolving, at 25° C., the polymeric components in a solution of buffer and denaturant.

CE sequencing runs for the separation media were conducted in the presence of a ladder of TET-dye labeled fragments, having lengths of 35, 50, 75, 100, 139, 150, 160, 200, 250, 300, 340, 350, 400, 450, 490, 500, 550, 600, 650 and 700 base pairs, at several temperatures, usually 50, 60 and 70° C., with 1.5 kV injection voltage and 10 sec injection time and with 9.5 kV run voltage. The crossover and run time were determined at each temperature.

The composition and CE sequencing performance data, from an average of data from four CE runs, for the separation media are summarized in Table 2.

TABLE 2

| CE Crossover and Run Time of Compositions of the Invention | | | | | | | |
|---|---|---|---|---|---|---|---|
| | PDMA | Crossover (bp) | | | Run Time for 700 bp (min) | | |
| PVF | (984 kDa) | 50° C. | 60° C. | 70° C. | 50° C. | 60° C. | 70° C. |
| IC1 | 2.23 wt % | 0.21 wt % | 620 | 615 | 485 | 54.7 | 51.2 | 49.4 |
| IC2 | 2.21 wt % | 0.20 wt % | 614 | 588 | 545 | 51.2 | 47.7 | 46.3 |
| IC3 | 2.17 wt % | 0.20 wt % | 590 | 552 | 482 | 47.1 | 43.2 | 40.9 |

The results in Table 2 demonstrate that the run times of each of IC1, IC2 and IC3 are advantageously short, e.g., at 50° C. Moreover, the results in Table 2 demonstrate that the crossover values of each of IC1, IC2 and IC3 are advantageously high, e.g., at 50° C. Accordingly, the compositions of the invention are useful for, e.g., the separation of a mixture of biomolecules.

5.3. Preparation of Illustrative Compositions of the Invention Comprising PMVA

Two compositions, IC4 and IC5, comprised poly(N-methyl-N-vinylacetamide) ("PMVA"). The weight percent for each of the components present in each composition is provided in Table 3.

TABLE 3

| Illustrative Compositions of the Invention Comprising PMVA | | |
|---|---|---|
| Composition Designation | IC4 | IC5 |
| PMVA Mw | 1420 kDa | 1420 kDa |
| PMVA Amount | 2.2% | 3.0% |
| 10X GA Buffer Amount | 9.0% | 9.1% |
| Urea Amount | 38.0% | 38.0% |
| MILLI-Q Water Amount | 50.6% | 49.9% |
| PDMA$^a$ Amount | 2.2% | 0% |

$^a$Mw = 984 kDa, Mn = 315 kDa

IC4 was prepared with dialyzed, lyophilized, substantially linear PDMA as described in Example 5.1. The water used in each of IC4-5 was purified using a MILLI-Q Water System. Each separation medium was prepared by dissolving, at 25° C., the polymeric components in a solution of buffer and denaturant.

5.4. Capillary Electrophoresis of DNA Using Compositions Comprising PMVA

Illustrative compositions of the invention IC4 and IC5 were evaluated for their DNA sequencing performance using CE as described in Example 5.2.

The composition and CE sequencing performance data, from an average of data from four CE runs, for the separation media are summarized in Table 4.

TABLE 4

| CE Crossover and Run Time of Compositions of the Invention | | | | | | | |
|---|---|---|---|---|---|---|---|
| PMVA | PDMA | Crossover (bp) | | | Run Time for 700 bp (min) | | |
| (1420 kDa) | (984 kDa) | 50° C. | 60° C. | 70° C. | 50° C. | 60° C. | 70° C. |
| IC4 | 2.2 wt % | 2.2 wt % | 546 | 466 | 359 | 38.1 | 36.3 | 37.7 |
| IC5 | 3.0 wt % | — | 550 | 479 | 384 | 46.9 | 44.7 | 46.2 |

The results in Table 4 demonstrate that the run times of each of IC4 and IC5 are advantageously short, e.g., at 50° C. Moreover, the results in Table 4 demonstrate that the crossover values of each of IC4 and IC5 are advantageously high, e.g., at 50° C. Accordingly, the compositions of the invention are useful for, e.g., the separation of a mixture of biomolecules.

Although the invention has been described with reference to particular embodiments, it will be appreciated that various changes and modifications can be made without departing from the spirit or scope of the invention.

All concentrations herein are by weight unless otherwise noted.

All publications and patent applications are herein incorporated by reference to the same extent as if each individual publication or patent application was specifically and individually indicated to be incorporated by reference.

What is claimed is:

1. A composition comprising a buffer and a polymer having the form poly($M_1^x M_2^y$), or a salt thereof, comprising one or more monomers of type M1 and optionally one or more monomers of type $M_2$, wherein:
   (a) each monomer in the polymer is of type $M_1$ or $M_2$;
   (b) x is an integer ranging from 1 to 5 and represents the number of monomer subtypes of type $M_1$ that are present in the polymer;
   (c) y is an integer ranging from 0 to 5 and represents the number of monomer subtypes of type $M_2$ that are present in the polymer;
   (d) each monomer subtype of type $M_1$ in the polymer is independently:
   N-vinylformamide, N-vinylacetamide, N-vinylpropamide, N-vinylbutamide, N-vinylpentamide, N-vinylhexamide, N-vinylheptamide, N-vinyloctamide, N-vinylnonamide, N-vinyldecamide, N-methyl-N-vinylformamide, N-methyl-N-vinylacetamide, N-methyl-N-vinylpropamide, N-methyl-N-vinylbutamide, N-methyl-N-vinylpentamide, N-methyl-N-vinylhexamide, N-methyl-N-vinylheptamide, N-methyl-N-vinyloctamide, N-methyl-N-vinylnonamide, N-methyl-N-vinyldecamide, N-ethyl-N-vinylformamide, N-ethyl-N-vinylacetamide, N-ethyl-N-vinylpropamide, N-ethyl-N-vinylbutamide, N-ethyl-N-vinylpentamide, N-ethyl-N-vinylhexamide, N-ethyl-N-vinylheptamide, N-ethyl-N-vinyloctamide, N-ethyl-N-vinylnonamide, N-ethyl-N-vinyldecamide, N-n-propyl-N-vinylformamide, N-n-propyl-N-vinylacetamide, N-n-propyl-N-vinyl propamide, N-n- propyl-N-vinylbutamide, N-n-propyl-N-vinylpentamide, N-n-propyl-N-vinylhexamide, N-n-propyl-N-vinylheptamide, N-n-propyl-N-vinyloctamide, N-n-propyl-N-vinylnonamide, N-n-propyl-N-vinyldecamide, N-iso-propyl-N-vinylformamide, N-iso-propyl-N-vinylacetamide, N-iso-propyl-N-vinylpropamide, N-iso-propyl-N-vinylbutamide, N-iso-propyl-N-vinylpentamide, N-iso-propyl-N-vinylhexamide, N-iso-propyl-N-vinylheptamide, N-isa-propyl-N-vinyloctamide, N-iso-propyl-N-vinylnonamide or N-iso-propyl-N-vinyldecamide;

(e) when y is not zero, each monomer subtype of type $M_2$ in the polymer is independently:

N-hydroxy-acrylamide, N-methoxy-acrylamide, acryloyl urea, 1-vinyl-pyrrolidine-2,5-dione, 3-vinyl-oxazolidin-2-one, 1-vinyl-imidazolidin-2-one, 4-vinyl-morpholin-3,5-dione, 4-vinyl-morpholin-3-one, 4-vinyl-morpholine, 2-vinyl-1,3-dioxolane, 2-vinylene carbonate, methoxyethylene, vinyl acetate, vinyl alcohol, acrylamide, N-acetamido-acrylamide, N-acetyl-acrylamide, N-allyl-acrylamide, N-2-aminoethyl-acrylamide hydrochloride, N-2-aminoethyl-N-methyl-acrylamide hydrochloride, N-3-aminopropyl-acrylamide hydrochloride, N-3-aminopropyl-N-methyl-aerylamide hydrochloride, N-butoxymethyl-acrylamide, N-n-butyl-acrylamide, N-tert-butyl-acrylamide, N-2-cyanoethyl-acrylamide, N-cyanomethyl-acrylamide, N-cyanomethyl-N-methyl-acrylamide, N,N-diallyl-acrylamide, N,N-diethyl-acrylamide, N,N-diisopropyl-acrylamide, N,N-dimethyl-acrylamide, N-ethyl-N-methyl-acrylamide, N-ethyl-N-propyl-acrylamide, N-2-glycolic acid-acrylamide, N-2-glycolic acid methyl ester-acrylamide, N-2-hydroxyethyl-acrylamide, N-2-hydroxyethyl-N-methyl-acrylamide, N-hydroxymethyl-acrylamide, N-hydroxymethyl-N-methyl-acrylamide, N-iso-propyl-acrylamide, N-2-methoxyethyl-acrylamide, N-methoxymethyl-acrylamide, N-methyl-acrylamide, N-2,2,2-trichloro-1-hydroxyethyl-acrylamide, N-tri(hydroxymethyl)methyl-acrylamide, N-tri(hydroxymethyl)methyl-N-methyl-acrylamide, N-3-(trimethylammonium)propyl-acrylamide hydrochloride, N-3-(trimethylammonium)propyl-N-methyl-acrylamide hydrochloride, methacrylamide, N-acetamido-methacrylamide, N-acetyl-methacrylamide, N-allyl-methacrylamide, N-2-aminoethyl-methacrylamide hydrochloride, N-3-aminopropyl-methacrylamide hydrochloride, N-butoxymethyl-methacrylamide, N-n-butyl-methacrylamide, N-tert-butyl-methacrylamide, N-2-cyanoethyl-methacrylamide, N-cyanomethyl-methacrylamide, N-cyanomethyl-N-methyl-methacrylamide, N,N-diethyl-methacrylamide, N,N-dimethyl-methacrylamide, N-2-glycolic acid-methacrylamide, N-2-hydroxyethyl-methacrylamide, N-hydroxymethyl-methacrylamide, N-hydroxymethyl-N-methyl-methacrylamide, N-iso-propyl-methacrylamide, N-2-methoxethyl-methacrylamide, N-methoxymethyl-methacrylamide, N-methyl-methacrylamide, N-tri(hydroxymethyl)methyl-methacrylamide, N-3-(trimethylammonium)propyl-methacrylamide hydrochloride, or a mixture thereof; and (f). further comprises an effective amount of a sieve and/or EOF suppressing polymer comprising a monomer unit that is acrylamide, N-acetyl-acrylamide, N-2-cyanoethyl-acrylamide, N,N-1,2-dihydroxyethylene-bis-acrylamide, N-4,4-dimethoxybutyl-acrylamide, N-2,2-dimethoxyethyl-acrylamide, N,N-dimethyl-acrylamide, N-2-glycolic acid methyl ester acrylamide, N-2-hydroxyethyl-acrylamide, N-hydroxymethyl-acrylamide, N-methoxymethyl-acrylamide, N-3-methoxypropyl-acrylamide, N-methyl-acrylamide, N-methyl-, N-2,2-dimethoxyethyl-acrylamide, N-morpholinoethyl-acrylamide, N-2,2,2-trichloro-1-hydroxyethyl-acrylamide, N-tri(hydroxymethyl)-methyl-acrylamide, methacrylamide, N-acetyl-methacrylamide, N-2-cyanoethyl-methacrylamide, N,N-1,2-dihydroxyethylene-bis-methacrylamide, N-4,4-dimethoxybutyl-methacrylamide, N-2,2-dimethoxyethyl-methacrylamide, N,N-dimethyl-methacrylamide, N-2-glycolic acid methyl ester methacrylamide, N-2-hydroxyethyl-methacrylamide, N-hydroxymethyl-methacrylamide, N-methoxymethyl-methacrylamide, N-3-methoxypropyl-methacrylamide, N-methyl-methacrylamide, N-methyl-, N-2,2-dimethoxyethyl-methacrylamide, N-morpholinoethyl-methacrylamide, N-2,2,2-trichloro-1-hydroxyethyl-methacrylamide, N-tri(hydroxymethyl)-methyl-methacrylamide, or a mixture thereof.

2. The composition of claim 1, wherein the sieve and/or EOF suppressing polymer monomer unit is acrylamide.

3. The composition of claim 1, which further comprises an effective amount of a sieve and/or EOF suppressing polymer which comprises or is poly(hydroxymethylene), poly(oxyethylene), poly(oxypropylene), poly(oxyethylene-co-oxypropylene), poly(vinylalcohol), poly(vinylpyrrolidone), poly(-ethyl-2-oxazoline), poly(-methyl-2-oxazoline), poly((2-ethyl-2-oxazoline)-co-(2-methyl-2-oxazoline)), poly(N-acetamidoacrylamide), poly(acryloxylurea), hydroxyethyl cellulose, hydroxymethyl cellulose, or a mixture thereof.

4. The composition of claim 1, wherein the polymer has a weight-average molecular weight of from about 150,000 Daltons to about 20 MDaltons.

5. The composition of claim 4, which further comprises an effective amount of a sieve and/or EOF suppressing polymer having a weight-average molecular weight of from about 1 MDalton to about 5 MDaltons.

6. The composition of claim 5, wherein the sieve and/or EOF suppressing polymer is substantially linear polyacrylamide.

7. The composition of claim 1, wherein the composition is an aqueous composition.

8. The composition of claim 7, wherein the composition has a pH of from about 5 to about 11.

9. The composition of claim 8, further comprising formamide, urea, pyrrolidone, N-methyl pyrrolidone, or a mixture thereof.

10. The composition of claim 9, further comprising urea.

11. The composition of claim 9, further comprising formamide.

12. The composition of claim 7, wherein the composition has a pH of from bout 7 to about 10.

13. The composition of claim 7, wherein y is 0 and each M1 is independently N-vinylformamide or N-methyl-N-vinylacetamide.

14. The composition of claim 1, wherein the composition is a dry composition.

15. The composition of claim 14, wherein the composition has a pH of from about 5 to about 11.

16. The composition of claim 15, further comprising formamide, urea, pyrrolidone, N-methyl pyrrolidone, or a mixture thereof.

17. The composition of claim 16, further comprising urea.

18. The composition of claim 16, further comprising formamide.

19. The composition of claim 14, wherein the composition has a pH of from about 7 to about 10.

20. The composition of claim 14, wherein y is 0 and each monomer subtype of type $M_1$ is independently N-vinylformamide or N-methyl-N-vinylacetamide.

21. A capillary containing composition of claim 1 comprising a buffer and a polymer having the form poly $(M_1^xM_2^y)$, or a salt thereof, comprising one or more monomers of type $M_1$ and optionally one or more monomers of type $M_2$, wherein:
   (a) each monomer in the polymer is of type $M_1$ or $M_2$;
   (b) x is an integer ranging from 1 to 5 and represents the number of monomer subtypes of type $M_1$ that are present in the polymer;
   (c) y is an integer ranging from 0 to 5 and represents the number of monomer subtypes of type $M_2$ that are present in the polymer;
   (d) each monomer subtype of type $M_1$ in the polymer is independently:
   N-vinylformamide, N-vinylacetamide, N-vinylpropamide, N-vinylbutamide, N-vinylpentamide, N-vinylhexamide, N-vinylheptamide, N-vinyloctamide, N-vinylnonamide, N-vinyldecamide, N-methyl-N-vinylformamide, N-methyl-N-vinylacetamide, N-methyl-N-vinylpropamide, N-methyl-N-vinylbutamide, N-methyl-N-vinylpentamide, N-methyl-N-vinylhexamide, N-methyl-N-vinylheptamide, N-methyl-N-vinyloctamide, N-methyl-N-vinylnonamide, N-methyl-N-vinyldecamide, N-ethyl-N-vinylformamide, N-ethyl-N-vinylacetamide, N-ethyl-N-vinylpropamide, N-ethyl-N-vinylbutamide, N-ethyl-N-vinylpentamide, N-ethyl-N-vinylhexamide, N-ethyl-N-vinylheptamide, N-ethyl-N-vinyloctamide, N-ethyl-N-vinylnonamide, N-ethyl-N-vinyldecamide, N-n-propyl-N-vinylformamide, N-n-propyl-N-vinylacetamide, N-n-propyl-N-vinylpropamide, N-n-propyl-N-vinylbutamide, N-n-propyl-N-vinylpentamide, N-n-propyl-N-vinylhexamide, N-n-propyl-N-vinylheptamide, N-n-propyl-N-vinyloctamide, N-n-propyl-N-vinylnonamide, N-n-propyl-N-vinyldecamide, N-iso-propyl-N-vinylformamide, N-iso-propyl-N-vinylacetamide, N-iso-propyl-N-vinylpropamide, N-iso-propyl-N-vinylbutamide, N-iso-propyl-N-vinylpentamide, N-iso-propyl-N-vinylhexamide, N-iso-propyl-N-vinylheptamide, N-isa-propyl-N-vinyloctamide, N-iso-propyl-N-vinylnonamide or N-iso-propyl-N-vinyldecamide;
   (e) when y is not zero, each monomer subtype of type $M_2$ in the polymer is independently:
   N-hydroxy-acrylamide, N-methoxy-acrylamide, acryloyl urea, 1-vinyl-pyrrolidine-2,5-dione, 3-vinyl-oxazolidin-2-one, 1-vinyl-imidazoli din-2-one, 4-vinyl-morpholin-3,5-dione, 4-vinyl-morpholin-3-one, 4-vinyl-morpholine, 2-vinyl-1,3-dioxolane, 2-vinylene carbonate, methoxyethylene, vinyl acetate, vinyl alcohol, acrylamide, N-acetamido-acrylamide, N-acetyl-acrylamide, N-allyl-acrylamide, N-2-aminoethyl-acrylamide hydrochloride, N-2-aminoethyl-N-methyl-acrylamide hydrochloride, N-3-aminopropyl-acrylamide hydrochloride, N-3-aminopropyl-N-methyl-aerylamide hydrochloride, N-butoxymethyl-acrylamide, N-n-butyl-acrylamide, N-tert-butyl-acrylamide, N-2-cyanoethyl-acrylamide, N-cyanomethyl-acrylamide, N-cyanomethyl-N-methyl-acrylamide, N,N-diallyl-acrylamide, N,N-diethyl-acrylamide, N,N-diisopropyl-acrylamide, N,N-dimethyl-acrylamide, N-ethyl-N-methyl-acrylamide, N-ethyl-N-propyl-acrylamide, N-2-glycolic acid-acrylamide, N-2-glycolic acid methyl ester-acrylamide, N-2-hydroxyethyl-acrylamide, N-2-hydroxyethyl-N-methyl-acrylamide, N-hydroxymethyl-acrylamide, N-hydroxymethyl-N-methyl-acrylamide, N-iso-propyl-acrylamide, N-2-methoxyethyl-acrylamide, N-methoxymethyl-acrylamide, N-methyl-acrylamide, N-2,2,2-trichloro-1-hydroxyethyl-acrylamide, N-tri(hydroxymethyl) methyl-acrylamide, N-tri(hydroxymethyl)methyl-N-methyl-acrylamide, N-3-(trimethylammonium)propyl-acrylamide hydrochloride, N-3-(trimethylammonium)propyl-N-methyl-acrylamide hydrochloride, methacrylamide, N-acetamido-methacrylamide, N-acetyl-methacrylamide, N-allyl-methacrylamide, N-2-aminoethyl-methacrylamide hydrochloride, N-3-aminopropyl-methacrylamide hydrochloride, N-butoxymethyl-methacrylamide, N-n-butyl-methacrylamide, N-tert-butvl-methacrylamide, N-2-cyanoethyl-methacrylamide, N-cyanomethyl-methacrylamide, N-cyanomethyl-N-methyl-methacrylamide, N,N-diethyl-methacrylamide, N,N-dimethyl-methacrylamide, N-2-glycolic acid-methacrylamide, N-2-hydroxyethyl-methacrylamide, N-hydroxymethyl-methacrylamide, N-hydroxymethyl-N-methyl-methacrylamide, N-iso-propyl-methacrylamide, N-2-methoxethyl-methacrylamide, N-methoxymethyl-methacrylamide, N-methyl-methacrylamide, N-tri(hydroxymethyl)methyl-methacrylamide, N-3-(trimethylammonium)propyl-methacrylamide hydrochloride, or a mixture thereof; and
   (f). further comprises an effective amount of a sieve and/or EOF suppressing polymer comprising a monomer unit that is acrylamide, N-acetyl-acrylamide, N-2-cyanoethyl-acrylamide, N,N-1,2-dihydroxyethylene-bis-acrylamide, N-4,4-dimethoxybutyl 1-acrylamide, N-2,2-dimethoxyethyl-acrylamide, N,N-dimethyl-acrylamide, N-2-glycolic acid methyl ester acrylamide, N-2-hydroxyethyl-acrylamide, N-hydroxymethyl-acrylamide, N-methoxymethyl-acrylamide, N-3-methoxypropyl-acrylamide, N-methyl-acrylamide, N-methyl-, N-2,2-dimethoxyethyl-acrylamide, N-morpholinoethyl-acrylamide, N-2,2,2-trichloro-1-hydroxyethyl-acrylamide, N-tri(hydroxymethyl)-methyl-acrylamide, methacrylamide, N-acetyl-methacrylamide, N-2-cyanoethyl-methacrylamide, N,N-1,2-dihydroxyethylene-bis-methacrylamide, N-4,4-dimethoxybutyl-methacrylamide, N-2,2-dimethoxyethyl-methacrylamide, N,N-dimethyl-methacrylamide, N-2-glycolic acid methyl ester methacrylamide, N-2-hydroxyethyl-methacrylamide, N-hydroxymethyl-methacrylamide, N-methoxymethyl-methacrylamide, N-3-methoxypropyl-methacrylamide, N-methyl-methacrylamide, N-methyl-, N-2,2-dimethoxyethyl-methacrylamide, N-morpholinoethyl-methacrylamide, N-2,2,2-trichloro-1 -hydroxyethyl-methacrylamide, N-tri(hydroxymethyl)-methyl-methacrylamide, or a mixture thereof.

22. The capillary of claim 21, wherein the capillary is a capillary tube.

23. A method for separating a mixture of biomolecules, comprising: (a) contacting the composition of claim 1 with a mixture comprising a biomolecule with a composition comprising a buffer and a polymer having the form poly $(M_1^x M_2^y)$, or a salt thereof, comprising one or more monomers of type $M_1$ and optionally one or more monomers of type $M_2$, wherein:
(a) each monomer in the polymer is of type $M_1$ or $M_2$;
(b) x is an integer ranging from 1 to 5 and represents the number of monomer subtypes of type $M_1$ that are present in the polymer;
(c) y is an integer ranging from 0 to 5 and represents the number of monomer subtypes of type $M_2$ that are present in the polymer;
(d) each monomer subtype of type $M_1$ in the polymer is independently:
N-vinylformamide, N-vinylacetamide, N-vinylpropamide, N-vinylbutamide, N-vinylpentamide, N-vinylhexamide, N-vinylheptamide, N-vinyloctamide, N-vinylnonamide, N-vinyl decamide, N-methyl-N-vinylformamide, N-methyl-N-vinylacetamide, N-methyl-N-vinylpropamide, N-methyl-N-vinylbutamide, N-methyl-N-vinylpentamide, N-methyl-N-vinylhexamide, N-methyl-N-vinylheptamide, N-methyl-N-vinyloctamide, N-methyl-N-vinylnonamide, N-methyl-N-vinyldecamide, N-ethyl-N-vinylformamide, N-ethyl-N-vinylacetamide, N-ethyl-N-vinylpropamide, N-ethyl-N-vinylbutamide, N-ethyl-N-vinylpentamide, N-ethyl-N-vinylhexamide, N-ethyl-N-vinylheptamide, N-ethyl-N-vinyloctamide, N-ethyl-N-vinylnonamide, N-ethyl-N-vinyldecamide, N-n-propyl-N-vinylformamide, N-n-propyl-N-vinylacetamide, N-n-propyl-N-vinylpropamide, N-n-propyl-N-vinylbutamide, N-n-propyl-N-vinylpentamide, N-n-propyl-N-vinylhexamide, N-n-propyl-N-vinylheptamide, N-n-propyl-N-vinyloctamide, N-n-propyl-N-vinylnonamide, N-n-propyl-N-vinyldecamide, N-iso-propyl-N-vinylformamide, N-iso-propyl-N-vinylacetamide, N-iso-propyl-N-vinylpropamide, N-iso-propyl-N-vinylbutamide, N-iso-propyl-N-vinylpentamide, N-iso-propyl-N-vinylhexamide, N-iso-propyl-N-vinylheptamide, N-isa-propyl-N-vinyloctamide, N-iso-propyl-N-vinylnonamide or N-iso-propyl-N-vinyldecamide; and
(e) when y is not zero, each monomer subtype of type $M_2$ in the polymer is independently: N-hydroxy-acrylamide, N-methoxy-acrylamide, acryloyl urea, 1-vinyl-pyrrolidine-2,5-dione, 3-vinyl -oxazolidin-2-one, 1-vinyl-imidazolidin-2-one, 4-vinyl-morpholin-3,5-dione, 4-vinyl-morpholin-3-one, 4-vinyl-morpholine, 2-vinyl-1,3-dioxolane, 2-vinylene carbonate, methoxyethylene, vinyl acetate, vinyl alcohol, acrylamide, N-acetamido-acrylamide, N-acetyl-acrylamide, N-allyl-acrylamide, N-2-aminoethyl-acrylamide hydrochloride, N-2-aminoethyl-N-methyl-acrylamide hydrochloride, N-3-aminopropyl-acrylamide hydrochloride, N-3-aminopropyl-N-methyl-aerylamide hydrochloride, N-butoxymethyl-acrylamide, N-n-butyl-acrylamide, N-tert-butyl-acrylamide, N-2-cyanoethyl-acrylamide, N-cyanomethyl-acrylamide, N-cyanomethyl-N-methyl-acrylamide, N,N-diallyl-acrylamide, N,N-diethyl-acrylamide, N,N-diisopropyl-acrylamide, N,N-dimethyl-acrylamide, N-ethyl-N-methyl-acrylamide, N-ethyl-N-propyl-acrylamide, N-2-glycolic acid-acrylamide, N-2-glycolic acid methyl ester-acrylamide, N-2-hydroxyethyl-acrylamide, N-2-hydroxyethyl-N-methyl-acrylamide, N-hydroxymethyl-acrylamide, N-hydroxymethyl-N-methyl-acrylamide, N-iso-propyl-acrylamide, N-2-methoxyethyl-acrylamide, N-methoxymethyl-acrylamide, N-methyl-acrylamide, N-2,2,2-trichloro-l-hydroxyethyl-acrylamide, N-tri(hydroxymethyl)methyl-acrylamide, N-tri(hydroxymethyl)methyl-N-methyl-acrylamide, N-3-(trimethylammonium)propyl-acrylamide hydrochloride, N-3-(trimethylammonium)propyl-N-methyl-acrylamide hydrochloride, methacrylamide, N-acetamido-methacrylamide, N-acetyl-methacrylamide, N-allyl-methacrylamide, N-2-aminoethyl-methacrylamide hydrochloride, N-3-aminopropyl-methacrylamide hydrochloride, N-butoxymethyl-methacrylamide, N-n-butyl-methacrylamide, N-tert-butvl-methacrylamide, N-2-cyanoethyl-methacrylamide, N-cyanomethyl-methacrylamide, N-cyanomethyl-N-methyl-methacrylamide, N,N-diethyl-methacrylamide, N,N-dimethyl-methacrylamide, N-2-glycolic acid-methacrylamide, N-2-hydroxyethyl-methacrylamide, N-hydroxymethyl-methacrylamide, N-hydroxymethyl-N-methyl-methacrylamide, N-iso-propyl-methacrylamide, N-2-methoxethyl-methacrylamide, N-methoxymethyl-methacrylamide, N-methyl-methacrylamide, N-tri(hydroxymethyl)methyl-methacrylamide, N-3-(trimethylammonium)propyl-methacrylamide hydrochloride, or a mixture thereof; and
(b) applying an electric field to the composition in an amount sufficient to facilitate the separation of a biomolecule from the mixture.

24. The method of claim 23, wherein the separation is performed within a capillary tube and two or more biomolecules are polynucleotides.

25. The method of claim 24, wherein the method for separating has a crossover of at least about 400 base pairs.

* * * * *